US009949725B2

(12) United States Patent
Stephens et al.

(10) Patent No.: US 9,949,725 B2
(45) Date of Patent: Apr. 24, 2018

(54) BIOPSY DEVICE WITH STRAINER

(71) Applicant: Devicor Medical Products, Inc., Cincinnati, OH (US)

(72) Inventors: Randy R. Stephens, Fairfield, OH (US); William A. Garrison, Springdale, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

(21) Appl. No.: 14/471,658

(22) Filed: Aug. 28, 2014

(65) Prior Publication Data

US 2014/0371625 A1    Dec. 18, 2014

Related U.S. Application Data

(60) Continuation of application No. 13/558,412, filed on Jul. 26, 2012, now Pat. No. 8,852,121, which is a continuation of application No. 12/896,071, filed on Oct. 1, 2010, now Pat. No. 8,257,275, which is a continuation of application No. 12/254,027, filed on Oct. 20, 2008, now Pat. No. 7,837,632, which is a
(Continued)

(51) Int. Cl.
*A61B 10/02* (2006.01)
*A61B 17/00* (2006.01)
*A61B 90/00* (2016.01)

(52) U.S. Cl.
CPC ...... *A61B 10/0266* (2013.01); *A61B 10/0275* (2013.01); *A61B 10/0283* (2013.01); *A61B 2010/0208* (2013.01); *A61B 2017/00398* (2013.01); *A61B 2017/00455* (2013.01); *A61B 2090/376* (2016.02)

(58) Field of Classification Search
CPC ............ A61B 10/0283; A61B 10/0275; A61B 10/0266; A61B 2090/376; A61B 2010/0208; A61B 2017/00398; A61B 2017/00455
USPC .................. 600/562–568; 606/167, 170, 171
See application file for complete search history.

(56) References Cited

U.S. PATENT DOCUMENTS 4,202,333 A * 5/1980 Thill et al. ..................... 604/135
4,699,154 A   10/1987 Lindgren
(Continued)

FOREIGN PATENT DOCUMENTS

EP          1642534 A2      4/2006
WO    WO 1998/033436       8/1998
(Continued)

OTHER PUBLICATIONS

Canadian Search Report dated Apr. 30, 2009 for Application No. CA 2,394,067, 3 pages.
(Continued)

*Primary Examiner* — Rene Towa
(74) *Attorney, Agent, or Firm* — Frost Brown Todd LLC

(57) ABSTRACT

The present application is directed to an image-guided, vacuum assisted, percutaneous, coring, cable driven breast biopsy instrument which may be conveniently mounted to an x-ray machine wherein the biopsy instrument incorporates a rotation knob at the proximal end of the instrument to manually rotate the distal end of the probe, thus allowing the clinician to conveniently position the tissue port next to the tissue to be sampled.

17 Claims, 17 Drawing Sheets

Related U.S. Application Data division of application No. 11/565,693, filed on Dec. 1, 2006, now Pat. No. 7,442,171, which is a division of application No. 10/454,064, filed on Jun. 3, 2003, now Pat. No. 7,153,274, which is a division of application No. 09/967,253, filed on Sep. 28, 2001, now Pat. No. 6,602,203.

(60) Provisional application No. 60/240,492, filed on Oct. 13, 2000.

(56) References Cited

U.S. PATENT DOCUMENTS

| | | | |
|---|---|---|---|
| 4,702,260 A | 10/1987 | Wang | |
| 4,944,308 A | 7/1990 | Akerfeldt | |
| 5,027,827 A | 7/1991 | Cody et al. | |
| RE34,056 E | 9/1992 | Lindgren et al. | |
| 5,183,052 A * | 2/1993 | Terwilliger | A61B 10/0283 600/566 |
| 5,429,138 A | 7/1995 | Jamshidi | |
| 5,492,130 A | 2/1996 | Chiou | |
| 5,526,821 A | 6/1996 | Jamshidi | |
| 5,526,822 A | 6/1996 | Burbank et al. | |
| 5,649,547 A | 7/1997 | Ritchart et al. | |
| 5,769,086 A | 6/1998 | Ritchart et al. | |
| 5,775,333 A | 7/1998 | Burbank et al. | |
| 5,830,152 A * | 11/1998 | Tao | A61B 10/0233 600/562 |
| 5,928,164 A | 7/1999 | Burbank et al. | |
| 5,980,469 A | 11/1999 | Burbank et al. | |
| 6,007,497 A * | 12/1999 | Huitema | A61B 10/0275 600/567 |
| 6,086,544 A * | 7/2000 | Hibner | A61B 10/0275 600/564 |
| 6,120,462 A | 9/2000 | Hibner et al. | |
| 6,142,955 A * | 11/2000 | Farascioni | A61B 10/0275 600/562 |
| 6,193,673 B1 * | 2/2001 | Viola et al. | 600/568 |
| 6,273,862 B1 | 8/2001 | Privitera et al. | |
| 6,602,203 B2 | 8/2003 | Stephens et al. | |
| 6,620,111 B2 | 9/2003 | Stephens et al. | |
| 7,153,274 B2 | 12/2006 | Stephens et al. | |
| 7,442,171 B2 | 10/2008 | Stephens | |
| 7,648,466 B2 | 1/2010 | Stephens et al. | |
| 7,837,632 B2 | 11/2010 | Stephens et al. | |
| 8,257,275 B2 | 9/2012 | Stephens et al. | |
| 8,852,121 B2 * | 10/2014 | Stephens | A61B 10/0275 600/567 |

FOREIGN PATENT DOCUMENTS

| | | |
|---|---|---|
| WO | WO 1999/065404 | 12/1999 |
| WO | WO 2000/030531 | 6/2000 |

OTHER PUBLICATIONS

U.S. Appl. No. 08/825,899, filed Apr. 2, 1997.
U.S. Appl. No. 60/240,492, filed Oct. 13, 2000.

* cited by examiner

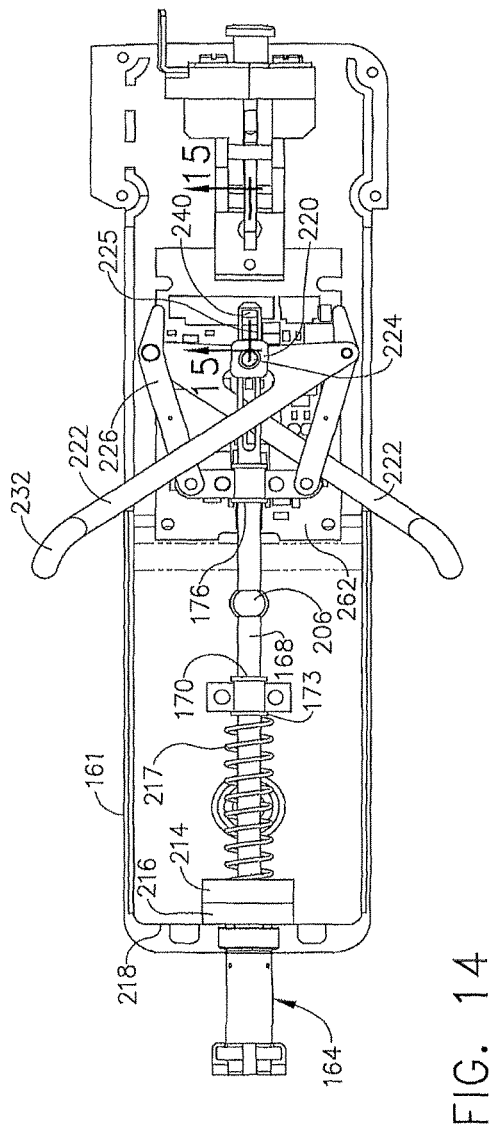
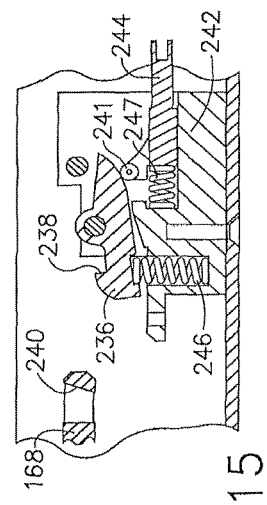
FIG. 14
FIG. 15

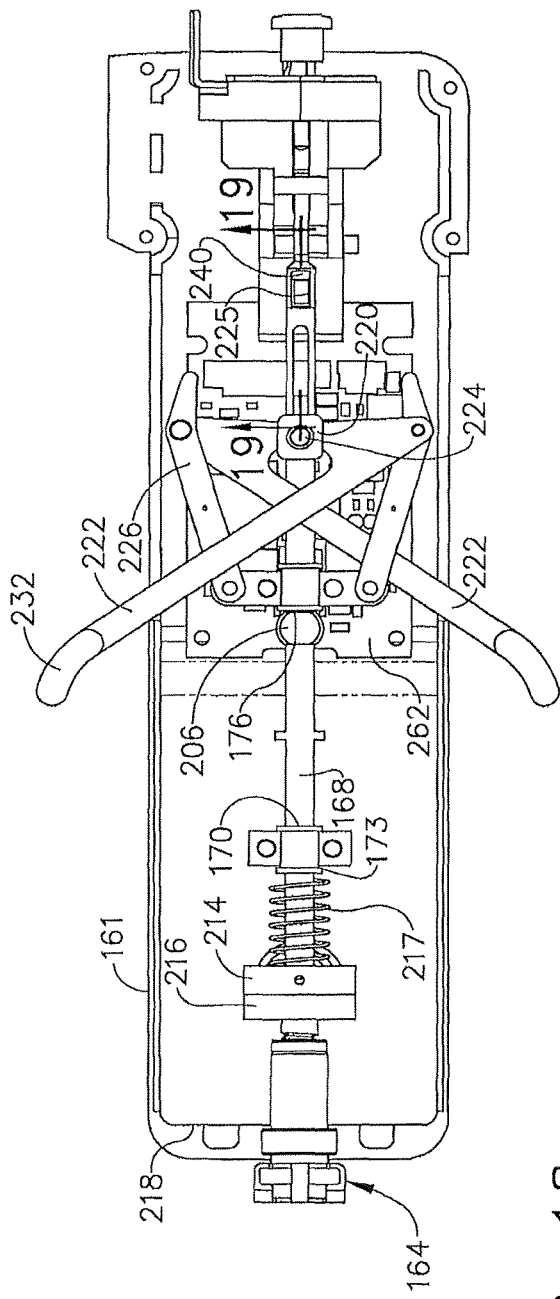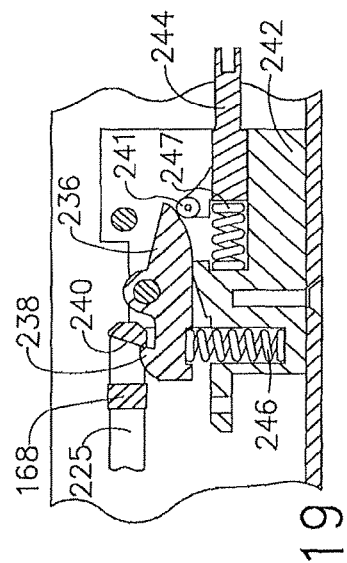
FIG. 18
FIG. 19

BIOPSY DEVICE WITH STRAINER

PRIORITY

This application is a continuation of U.S. patent application Ser. No. 13/558,412, filed Jul. 26, 2012, which is a continuation of U.S. patent application Ser. No. 12/896,071, filed Oct. 1, 2010, now U.S. Pat. No. 8,257,275, which is a continuation of U.S. patent application Ser. No. 12/254,027, filed Oct. 20, 2008, now U.S. Pat. No. 7,837,632, which is a divisional of U.S. patent application Ser. No. 11/565,693, filed Dec. 1, 2006, now U.S. Pat. No. 7,442,171, which is a divisional of U.S. patent application Ser. No. 10/454,064, filed Jun. 3, 2003, now U.S. Pat. No. 7,153,274, which is a divisional of U.S. patent application Ser. No. 09/967,253, filed Sep. 28, 2001, now U.S. Pat. No. 6,602,203, which claims the benefit of U.S. Provisional Application No. 60/240,492, filed Oct. 13, 2000.

FIELD OF THE INVENTION

The present invention relates, in general, to an improved surgical biopsy instrument and, more particularly, to a remote thumbwheel mechanism for use in a surgical biopsy instrument.

BACKGROUND OF THE INVENTION

The diagnosis and treatment of patients with cancerous tumors, pre-malignant conditions, and other disorders has long been an area of intense interest in the medical community. Non-invasive methods for examining tissue and, more particularly, breast tissue include palpation, X-ray imaging, MRI imaging, CT imaging, and ultrasound imaging. When a physician suspects that tissue may contain cancerous cells, a biopsy may be done using either an open procedure or in a percutaneous procedure. In an open procedure, a scalpel is used by the surgeon to create an incision to provide direct viewing and access to the tissue mass of interest. The biopsy may then be done by removal of the entire mass (excisional biopsy) or a part of the mass (incisional biopsy). In a percutaneous biopsy, a needle-like instrument is inserted through a very small incision to access the tissue mass of interest and to obtain a tissue sample for examination and analysis. The advantages of the percutaneous method as compared to the open method are significant: less recovery time for the patient, less pain, less surgical time, lower cost, less disruption of associated tissue and nerves and less disfigurement. Percutaneous methods are generally used in combination with imaging devices such as X-ray and ultrasound to allow the surgeon to locate the tissue mass and accurately position the biopsy instrument.

Generally there are two ways to percutaneously obtain a tissue sample from within the body, aspiration or core sampling, Aspiration of the tissue through a fine needle requires the tissue to be fragmented into small enough pieces to be withdrawn in a fluid medium. Application is less intrusive than other known sampling techniques, but one can only examine cells in the liquid (cytology) and not the cells and the structure (pathology). In core biopsy, a core or fragment of tissue is obtained for histologic examination which may be done via a frozen or paraffin section. The type of biopsy used depends mainly on various factors and no single procedure is ideal for all cases.

A number of core biopsy instruments which may be used in combination with imaging devices are known. Spring powered core biopsy devices are described and illustrated in U.S. Pat. Nos. 4,699,154, 4,944,308, and Re. 34,056. Aspiration devices are described and illustrated in U.S. Pat. Nos. 5,492,130; 5,526,821; 5,429,138 and 5,027,827.

U.S. Pat. No. 5,526,822 describes and illustrates an image-guided, vacuum-assisted, percutaneous, coring, breast biopsy instrument which takes multiple tissue samples without having to re-puncture the tissue for each sample. The physician uses this biopsy instrument to "actively" capture (using the vacuum) the tissue prior to severing it from the body. This allows the physician to sample tissues of varying hardness. The instrument described in U.S. Pat. No. 5,526,822 may also be used to collect multiple samples in numerous positions about its longitudinal axis without removing the instrument from the body. A further image-guided, vacuum-assisted, percutaneous, coring, breast biopsy instrument is described in commonly assigned U.S. Ser. No. 08/825,899, filed on Apr. 2, 1997 and in U.S. Pat. Nos. 6,007,497; 5,649,547; 5,769,086; 5,775,333; and 5,928,164. A handheld image-guided, vacuum-assisted, percutaneous, coring, breast biopsy instrument is described in U.S. Pat. No. 6,086,544 and in U.S. Pat. No. 6,120,462. The instrument described therein moves drive motors and other electronic components into a control unit separate from and remotely located from the biopsy probe. Biopsy probe cutter rotational and translational motion is transferred from the motors in the control unit to the biopsy probe via flexible coaxial cables. This arrangement improves the cleanability of the reusable hardware that remains in close proximity to the, biopsy site as well as improves the life and durability of the electric motors and electronic components now remotely located from the biopsy probe. The biopsy instrument described and illustrated in U.S. Pat. No. 6,086,544 and in U.S. Pat. No. 6,120,462 was designed primarily to be a "hand held" instrument to be used by the clinician in conjunction with real time ultrasound imaging. Several image-guided, vacuum-assisted, percutaneous, coring, breast biopsy instruments are currently sold by Ethicon Endo-Surgery, Inc. under the Trademark MAMMOTOME™

The majority of breast biopsies done today, however, utilize an x-ray machine as the imaging modality. Using x-ray requires that the biopsy instrument be affixed to the x-ray machine by some type of bracket arrangement. Since the biopsy instrument is fixed to a portion of the x-ray machine there is now a need for a means to conveniently rotate the biopsy probe once it is advanced into the breast in order to accurately position the vacuum port at the distal end of the probe.

In U.S. Pat. No. 5,769,086 a biopsy probe is disclosed which includes an electric motor, connected to the proximal end of the biopsy probe via a gear train. Activating the motor causes rotation of the piercing element of the biopsy probe so that multiple tissue specimens may be obtained by the clinician at any location around the center axis of the probe. U.S. Pat. No. 5,649,547 illustrates and describes a biopsy instrument which includes a "thumb wheel" at the proximal end of the biopsy probe piercing element. The thumb wheel provides a convenient place for the clinician to grasp the piercing element to manually rotate the biopsy probe about its center axis so that multiple tissue samples could be taken at any position, as determined by the clinician, about the axis of the probe. There are a couple of problems, however, that become evident when this arrangement is put into clinical use. First, when the biopsy probe is used in combination with and mounted to an x-ray machine, it can be difficult for the clinician to get access to the thumb wheel portion of the biopsy probe because of brackets, hoses, and other obstructions in the area around the probe.

It would, therefore, be advantageous to design an image-guided, vacuum assisted, percutaneous, coring, cable driven breast biopsy instrument which may be conveniently mounted to an x-ray machine, and incorporate in it a remotely located means to manually rotate the probe, located in an area away from the surgical site and easily accessible by the clinician. It would further be advantageous to design an image-guided, vacuum assisted, percutaneous, coring, cable driven breast biopsy instrument which may be conveniently mounted to an x-ray machine which would incorporate a port rotation knob located at the proximal end of the biopsy instrument.

SUMMARY OF THE INVENTION

The present invention is directed to a biopsy instrument including a base assembly including a firing mechanism movably attached to a distal end of the base assembly, a probe assembly detachably mounted to the base assembly and a drive assembly detachably mounted to the cutter assembly and including a flexible drive shaft operatively connected to the cutter. The probe assembly including a piercer assembly and a cutter assembly detachably affixed to the base assembly. The piercer assembly including a piercer and a probe mount supporting the piercer. The piercer including a distal port, a vacuum lumen, a cutter lumen and a first gear mechanism affixed to a proximal end of the piercer. The cutter assembly includes a cutter adapted to move through the cutter lumen, an adjustment wheel extending from a proximal end of the cutter assembly and a drive rod connected to the adjustment wheel, the drive rod being operatively connected to the first gear mechanism.

The present invention is further directed to a biopsy instrument including a base assembly including a firing mechanism moveably attached to a distal end of the base assembly, a probe assembly moveably attached to the base assembly and a drive assembly detachably mounted to the cutter assembly, the drive assembly including a flexible drive shaft operatively connected to the cutter. The probe assembly including a piercer assembly which includes a piercer moveable from a proximal position to a distal position, a probe mount supporting the piercer and a cutter assembly detachably affixed to the base assembly. The piercer including a distal port, a vacuum port, a cutter lumen and a first gear affixed to a proximal end of the piercer. The probe mount including a second gear affixed to a drive shaft and the second gear meshing with the first gear and a fork coupling detachably mountable to the firing mechanism. The cutter assembly including a cutter adapted to move through the cutter lumen, an adjustment wheel extending from a proximal end of the cutter assembly and a drive rod connected to the adjustment wheel, the drive rod being slideably affixed to a proximal end of the drive shaft such that rotation of the adjustment wheel rotates the piercer as the piercer moves from the proximal position to the distal position.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 14 is a top view of the firing mechanism of the present invention showing the mechanism in the post-fired position.

FIG. 15 is a partial, plan sectional view of the firing mechanism in the post-fired position showing the firing latch and firing rod.

FIG. 18 is a top view of the firing mechanism of the present invention showing the arming mechanism in the relaxed position.

FIG. 19 is a partial, plan sectional view of the firing mechanism in the relaxed position showing the firing latch and firing rod.

DETAILED DESCRIPTION OF THE INVENTION

Figure 1:
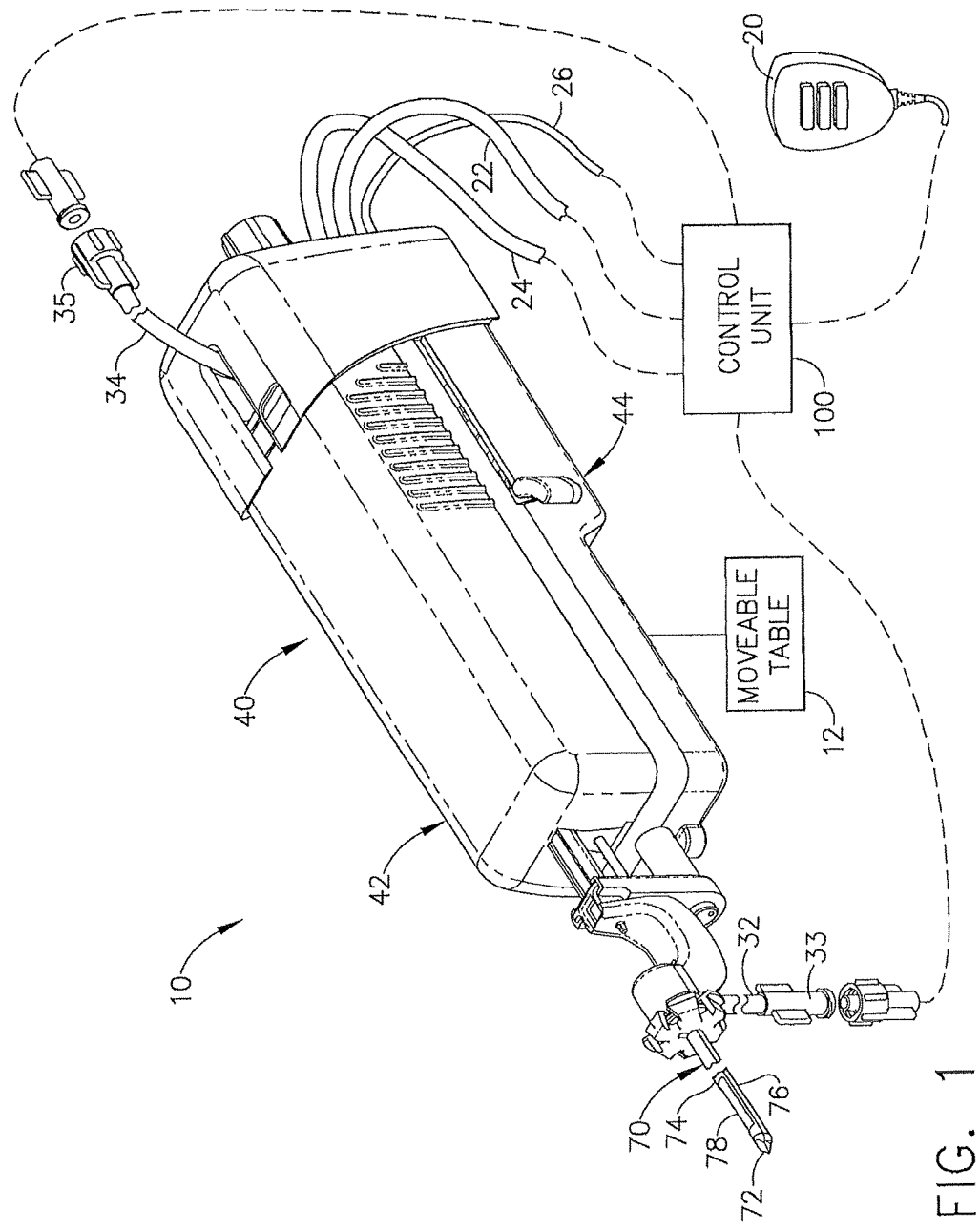
FIG. 1 is an isometric view of a surgical biopsy system of the present invention comprising a biopsy device, control unit, and remote.

FIG. 1 is an isometric view showing a surgical biopsy system 10 comprising biopsy device 40, a control unit 100, and remote 20. Biopsy device 40 comprises probe assembly 42 operatively and removably attached to base 44. Base 44 is removably attached to a moveable table 12 such as a stereotactic guidance system as may be found on mammographic x-ray machines, an example of which is Model MAMMOTEST PLUS/S available from Fischer Imaging, Inc., Denver, Colo.

Probe assembly 42 includes an elongated piercer 70 having a piercer tip 72 for penetrating soft tissue of a surgical patent. Piercer 70 comprises a piercer tube 74 and vacuum chamber tube 76. Vacuum chamber tube 76 of piercer 70 may be fluidly connected to control unit 100. Similarly, axial vacuum to probe assembly 42 may be obtained by fluid connection to control unit 100. MAMMOTOME™ system tubing set Model No. MVAC1 available from Ethicon Endo-Surgery Inc., Cincinnati, Ohio is suitable for use to permit detachable fluid connection of lateral vacuum line 32 and axial vacuum line 34 to control unit 100. Lateral vacuum line 32 and axial vacuum line 34 are made from a flexible, transparent or translucent material, such as silicone tubing, allowing for visualization of the material flowing through them. Lateral connector 33 and axial connector 35 are female and male luer connectors, respectively, commonly known and used in the medical industry. Base 44 is operatively connected to control unit 100 by control cord 26, translation shaft 22, and rotation shaft 24. Translation shaft 22 and rotation shaft 24 are preferably flexible so as to permit for ease of mounting of biopsy device 40 to moveable table 12.

Control unit 100 is used to control the sequence of actions performed by biopsy device 40 in order to obtain a biopsy sample from a surgical patient. Control unit 100 includes motors and a vacuum pump, and controls the activation of vacuum to probe assembly 42 and the translation and rotation of the cutter (not visible) in probe assembly 42. A suitable Control unit 100 is a MAMMOTOME™ system control module Model No. SCM12 with software Model No. SCMS1 available from Ethicon Endo-Surgery Inc., Cincinnati, Ohio.

Remote 20 is operatively and removably connected to control unit 100. Remote 20 may be used by the surgical biopsy system operator to control the sequence of actions performed by biopsy device 40. Remote 20 may be a hand operated or foot operated device. A suitable remote 20 is MAMMOTOME™ Remote Key-pad Model No. MKEY1 available from Ethicon Endo-Surgery Inc., Cincinnati, Ohio.

Figure 2:
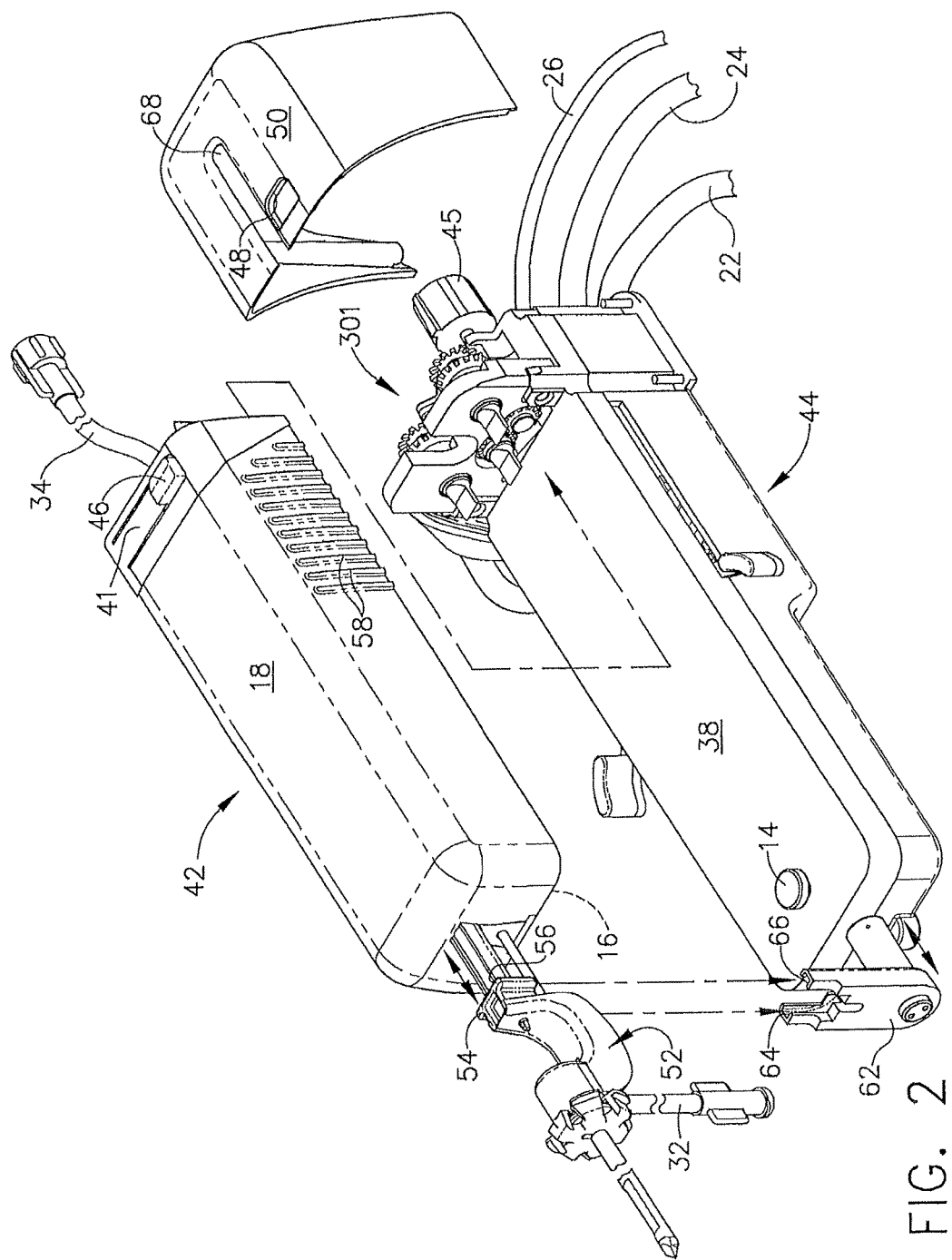
FIG. 2 is an isometric view of the biopsy probe assembly and base assembly, shown separated, with the upper base housing shown removed.

FIG. 2 is an isometric view showing probe assembly 42 and base 44 separated. Upper base housing 50 is normally fixedly attached to base 44, but has been shown removed from base 44 to provide a view of transmission 301. Top shell tab 46 is located on the distal end of cantilever beam 41 and projects above the top surface of gear shell 18. Top shell tab 46 inserts into tab window 48 in upper base housing 50 upon assembly of probe assembly 42 to base 44. Once probe assembly 42 and base 44 are properly assembled, top shell tab 46 must be pushed down through tab window 48 by the user before probe assembly 42 and base 44 can be separated. A plurality of raised ribs 58 is provided on gear shell 18 to improve the user's grip on the instrument. Post 14 extends above the top surface of base shell 38 and inserts into keyhole 16 (not visible) located on the underside of gear shell 18. Tube slot 68 in upper base housing 50 provides clearance for axial vacuum line 34, First tang 54 and second tang 56 protrude from opposite sides of probe housing 52 and insert into first recess 64 and second recess 66, respectively, in firing fork 62. The proximal end of probe housing 52 fits slidably within gear shell 18 and firing fork 62 fits slidably within base shell 38. Thus, once probe assembly 42 and base 44 are operatively assembled, probe housing 52 and firing fork 62 are able to move a fixed linear distance in a distal and proximal direction in front of gear shell 18 and base shell 38. FIGS. 1 and 2 show probe housing 52 and firing fork 62 in their most distal position.

Figure 3:
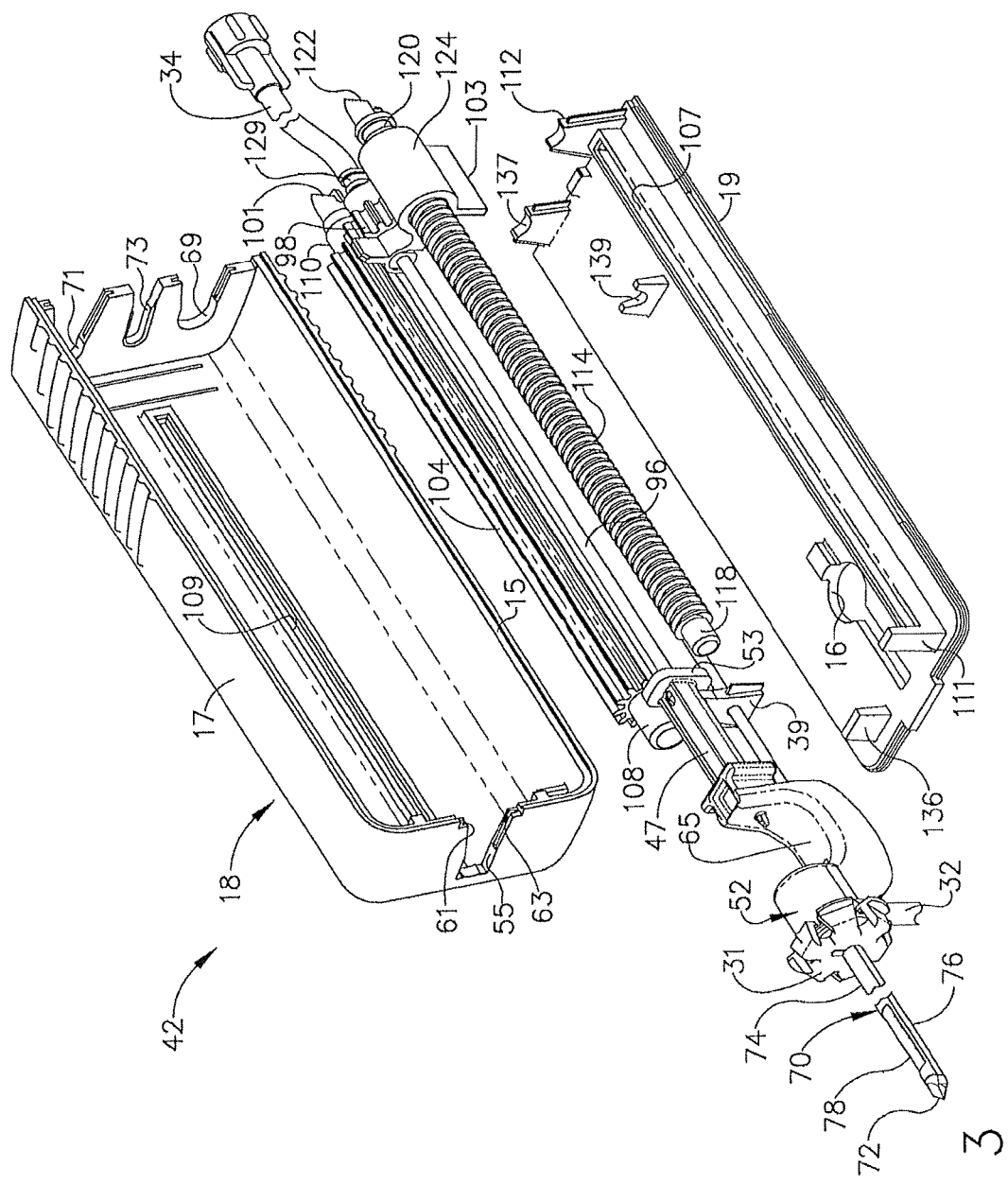
FIG. 3 is an isometric view of the biopsy probe assembly with the top shell and bottom shell shown separated to expose internal components.
Figure 4:
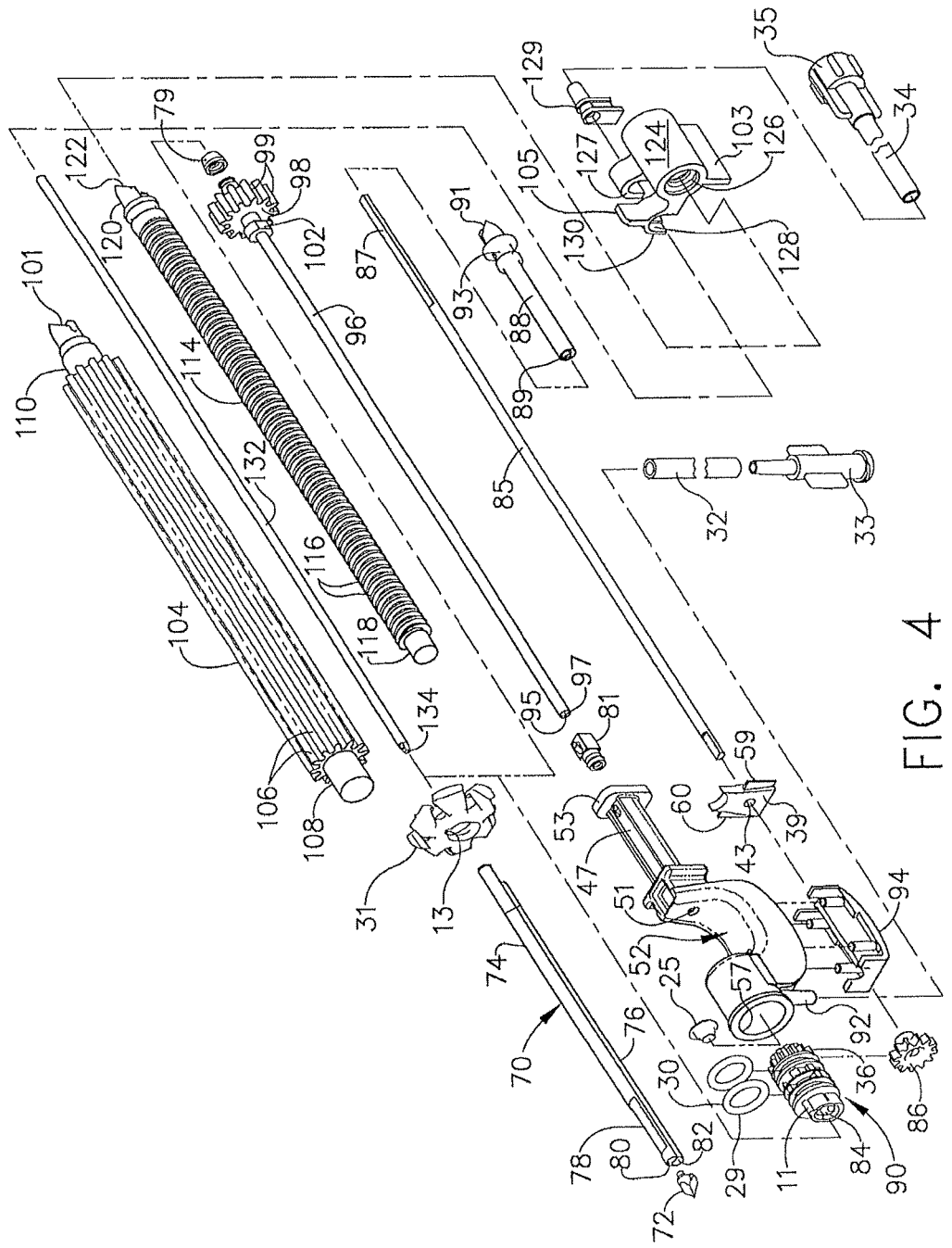
FIG. 4 is an exploded isometric view of the biopsy probe assembly of the present invention without the top shell and bottom shell.

FIGS. 3 and 4 are views of probe assembly 42. FIG. 3 is an isometric view of probe assembly 42 with the top shell 17 and bottom shell 19 shown separated, the top shell 17 rotated ninety degrees, to expose internal components. FIG. 4 is an exploded isometric view of the same probe assembly 42 without top shell 17 or bottom shell 19. Gear shell 18 is formed from top shell 17 and bottom shell 19, each injection molded from a rigid, biocompatible thermoplastic material such as polycarbonate. Upon final assembly of probe assembly 42, top shell 17 and bottom shell 19 are joined together by ultrasonic welding along joining edge 15, or joined by other methods well known in the art. Probe assembly 42 comprises piercer 70 having an elongated, metallic piercer tube 74 and a piercer lumen 80 (see FIGS. 4 and 5). On the side of the distal end of piercer tube 74 is port 78 for receiving tissue to be extracted from the surgical patient. Joined along side piercer tube 74 is an elongated, tubular, metallic vacuum chamber tube 76 having a vacuum lumen 82 (see FIGS. 4 and 5). Piercer lumen 80 is in fluid connection with vacuum lumen 82 via a plurality of vacuum holes 77 (See FIG. 5) located in the bottom of the "bowl" defined by port 78. Vacuum holes 77 are small enough to remove the fluids but not large enough to allow excised tissue portions to be removed through lateral vacuum line 32, which is fluidly connected to vacuum lumen 82. A metallic, sharpened piercer tip 72 is fixedly attached to the distal end of piercer 70. It is designed to penetrate soft tissue, such as the breast tissue of a female surgical patient. In the present embodiment piercer tip 72 is a three sided, pyramidal shaped point, although the tip configuration may also have other shapes.

Figure 5:
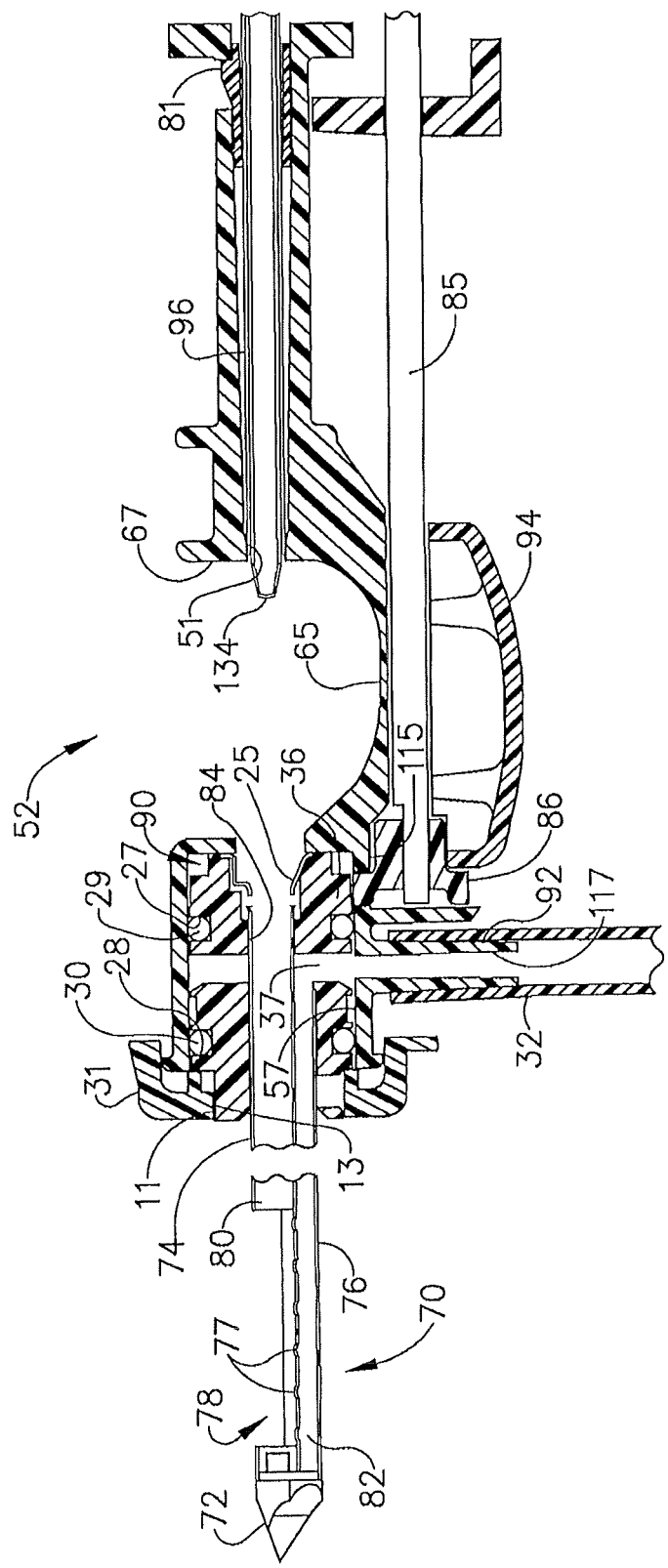
FIG. 5 is a longitudinal section view of the distal end of the biopsy probe assembly.

Refer now, momentarily, to FIG. 5. FIG. 5 is a section view of the distal end of probe assembly 42, illustrating primarily probe housing 52, piercer 70, and union sleeve 90. The proximal end of piercer 70 is fixedly attached to union sleeve 90 having a longitudinal bore 84 through it. Union sleeve 90 contains a first o-ring groove 27 and second o-ring groove 28, spaced apart so as to allow for a traverse opening 37 between them in fluid communication with longitudinal bore 84. First o-ring 29 and second o-ring 30 mount in first o-ring groove 27 and second o-ring groove 28, respectively. Sleeve gear 36 is integral to union sleeve 90 and is located at its most proximal end. Lead-in cone 25 is a conical shaped metallic structure that attaches to the proximal end of union sleeve 90. Union sleeve 90 is inserted into housing bore 57 located in the distal end of probe housing 52, and rotatably supports the proximal end of piercer 70. Positioning wheel 31 slides over piercer 70 and the distal end of union sleeve 90 and rotatably attaches to probe housing 52, hence trapping lead-in cone 25 and union sleeve 90 within housing bore 57 in the distal end of probe housing 52. Locating projection 11 on the distal end of union sleeve 90 functionally engages alignment notch 13 in positioning wheel 31. Thus, rotating positioning wheel 31 likewise causes the rotation of piercer 70. This allows port 78 to be readily positioned anywhere within the 360.degree. axis of rotation of piercer 70.

Referring again to FIGS. 3 and 4, housing extension 47 is located at the proximal end of probe housing 52. Housing flange 53 is located at the most proximal end of housing extension 47 on probe housing 52 and is assembled just inside of top shell front slot 55 in top shell 17. Shell insert 39 is assembled into top shell front slot 55. First insert tab 59 and second insert tab 60, both located on shell insert 39, engage first shell recess 61 and second shell recess 63, located within top shell front slot 55, respectively. Thus, upon complete assembly of probe assembly 42, the most proximal end of probe housing 52 containing housing flange 53 is trapped within gear shell 18, yet slideable along housing extension 47 distal and proximal within top shell front slot 55. Tissue sampling surface 65 is a recessed surface within probe housing 52 which provides a surface where each tissue sample will be deposited during the operation of the present invention, prior to retrieval by the clinician.

An elongated, metallic, tubular cutter 96 (see FIG. 5) is axially aligned within cutter bore 51 of probe housing 52, longitudinal bore 84 of union sleeve 90, and piercer lumen 80 of piercer 70 so that cutter 96 may slide easily in both the distal and proximal directions. Cutter 96 has a cutter lumen 95 through the entire length of cutter 96. The distal end of cutter 96 is sharpened to form a cutter blade 97 for cutting tissue held against cutter blade 97 as cutter 96 is rotated. The proximal end of cutter 96 is fixedly attached to the inside of cutter gear bore 102 of cutter gear 98. Cutter gear 98 may be metal or thermoplastic, and has a plurality of cutter gear teeth 99, each tooth having a typical spur gear tooth configuration as is well known in the art. Cutter seal 79 is a lip type seal and is fixedly attached to the proximal end of cutter gear 98, and is made of a flexible material such as silicone. Tissue remover 132 fits rotatably and slidably through cutter seal 79. Probe seal 81 is also a lip type seal made of a flexible material such as silicone rubber and is fixedly inserted into the proximal end of cutter bore 51 at the proximal end of probe housing 52. Cutter 96 fits rotatably and slidably through cutter seal 79. Cutter seal 79 and probe seal 81 operate to prevent fluids from entering the space within gear shell 18 during a surgical biopsy procedure.

Still in FIGS. 3 and 4, cutter gear 98 is driven by elongated drive gear 104 having a plurality of drive gear teeth 106 designed to mesh with cutter gear teeth 99. The function of elongated drive gear 104 is to rotate cutter gear 98 and cutter 96 as they translate in both longitudinal directions. Elongated drive gear 104 is preferably made of a thermoplastic material, such as liquid crystal polymer.

Distal drive axle 108 projects from the distal end of elongated drive gear 104 and mounts rotatably into an axle support rib (not visible) molded on the inside of top shell 17 and held in place by first gear support rib located on bottom shell 19. Gear shaft 110 projects from the proximal end of drive gear 104 and is rotatably supported by a gear shaft slot 69 located in the proximal end of top shell 17 and by second gear support rib 137 located on bottom shell 19. Drive gear slot 101 is located on the most proximal end of gear shaft 110 as a means for rotationally engaging drive gear 104.

Still referring to FIGS. 3 and 4, cutter carriage 124 is provided to hold cutter gear 98 and to carry cutter gear 98 as it is rotated and translated in the distal and proximal directions. Cutter carriage 124 is preferably molded from a thermoplastic material and is generally cylindrically shaped with a threaded bore 126 through it and with carriage foot 130 extending from its side. Carriage foot 130 has a foot recess 128 formed into it and foot slot 127 for rotatably holding cutter gear 98 in the proper orientation for cutter gear teeth 99 to mesh properly with drive gear teeth 106. Lower carriage guide 103 projects down from cutter carriage 124 and slidably engages lower guide slot 107 molded on the inside surface of bottom shell 19. Upper carriage guide 105 projects up from carriage foot 130 and slidably engages a upper guide slot 109 molded on the inside of top shell 17. Cutter carriage 124 is attached via threaded bore 126 to elongated screw 114, which is parallel to drive gear 104. Screw 114 has a plurality of conventional lead screw threads 116 and is preferably made of a thermoplastic material. The rotation of elongated screw 114 in one direction causes cutter carriage 124 to move distally, while the reverse rotation of elongated screw 114 causes cutter carriage 124 to move proximally. As a result, cutter gear 98 moves distally and proximally according to the direction of the screw rotation, which in turn advances cutter 96 distally or retracts it proximally. In the present embodiment, elongated screw 114 is shown with a right hand thread so that clockwise rotation (looking from the proximal to distal direction) causes cutter carriage 124 to translate in the proximal direction. Distal screw axle 118 projects from the distal end of elongated screw 114 and mounts rotatably into an axle support rib (not visible) molded on the inside of top shell 17 and held in place by first screw support rib 111 located on bottom shell 19. Screw shaft 120 projects from the proximal end of elongated screw 114 and is rotatably supported by a screw shaft slot 71 located in the proximal end of top shell 17 and by second screw support rib 112 located on bottom shell 19. Lead screw slot 122 is located on the most proximal end of screw shaft 120 as a means for rotationally engaging elongated screw 114.

At this point in the detailed description it should be pointed out that during the operation of the biopsy instrument cutter 96 translates in either direction between a fully retracted position, just proximal to tissue sampling surface 65 as referenced by cutter blade 97, and a fully deployed position wherein cutter blade 97 is located just distal to port 78. As cutter 96 translates between these end points there are a number of intermediate positions wherein adjustments may be made to the cutter rotational and translational speed as commanded by control unit 100. These intermediate positions and the adjustments made to the cutter depend on the programming of control unit 100.

Referring now to FIG. 5, the distal end of lateral vacuum line 32 is attached to lateral fitting 92 located on the distal end of probe housing 52. Lateral fitting 92 has lateral hole 117 through it along its axis in fluid communication with housing bore 57. Lateral hole 117 in lateral fitting 92 is positioned within housing bore 57 such that when union sleeve 90 is inserted into housing bore 57 lateral hole 117 is located in the space created between first and second o-rings, 29 and 30 respectively. Locating lateral hole 117 in the space between first and second o-rings 29 and 30, respectively, allows for the communication of fluids between vacuum lumen 82 and control unit 100.

Referring again to FIGS. 3 and 4, axial vacuum line 34 is fluidly attached to tissue remover support 129 which is in turn fluidly attached to the proximal end of an elongated, metallic, tubular tissue remover 132. Axial vacuum line 34 allows for the communication of fluids between piercer lumen 80, cutter lumen 95, and control unit 100. Tissue remover support 129 fits into axial support slot 73 located in the proximal end of top shell 17. Strainer 134 is located on the distal end of tissue remover 132 and functions to prevent passage of fragmented tissue portions through it and into control unit 100. Tissue remover 132 inserts slidably into cutter lumen 95 of cutter 96. During the operation of the biopsy instrument, tissue remover 132 is always stationary, being fixedly attached at its proximal end to tissue remover support 129 which is fixed within axial support slot 73 located in the proximal end of top shell 17. When cutter 96 is fully retracted to its most proximal position, the distal end of tissue remover 132 is approximately even with the distal end of cutter 96 (see FIG. 5). The distal end of cutter 96, when at its most proximal position, and probe housing 52 at its most distal position, is slightly distal to housing wall 67 which is proximal and perpendicular to tissue sampling surface 65.

Probe rotation rod 85 is an elongated, solid metal rod. Rotation rod gear 86 is a spur gear fixedly attached to the distal end of probe rotation rod 85. Rotation rod flat 87 is located at the proximal end of probe rotation rod 85. Rotation rod flat 87 is approximately one-third to one-half the rod diameter in depth and extending from its proximal end approximately one inch in length. Rotation rod flat 87 thus creates a "D" shaped geometry at the proximal end of probe rotation rod 85. Rod bushing 88 is made of molded thermoplastic and is cylindrical in shape. At its distal end is bushing bore 89 which is a "D" shaped hole approximately one inch in depth, designed to slidably receive the proximal end of probe rotation rod 85. Rod bushing 88 fits rotatably into axial support slot 73 below tissue remover support 129 at the proximal end of top shell 17. The longitudinal position of rod bushing 88 is fixed by the raised sections on both sides of bushing groove 93, upon assembly into the proximal end of top shell 17. Rod bushing drive slot 91 is located on the most proximal end of rod bushing 88 as a means for rotationally engaging rod bushing 88. Rotation gear 86 is rotatably fixed into gear cavity 115 on the underside of probe housing 52, the opening being in communication with housing bore 57 (see FIG. 5). Rotation rod gear 86 operably engages sleeve gear 36 located at the proximal end of union sleeve 90. The distal end of probe rotation rod 85 with rotation rod gear 86 attached is rotatably fixed to the underside of probe housing 52 by rotation gear cover 94. Rotation gear cover 94 is molded from a thermoplastic material and is fixedly attached to probe housing 52 by four raised cylindrical pins which press fit into four holes (not visible) in probe housing 52. Probe rotation rod 85 inserts rotatably and slidably through rod hole 43 in shell insert 39. The proximal end of probe rotation rod 85 slidably engages bushing bore 89 in rod bushing 88. Thus, rotation of rod bushing 88 causes rotation of probe rotation rod 85 which is fixedly attached to rotation rod gear 86 causing rotation of union sleeve 90 which is fixedly attached to piercer 70, which contains port 78.

It is important for the user of the surgical biopsy system of the present invention to be able to "fire" the piercer 70 into the tissue of a surgical patient. It is also important that the user be able to rotate piercer 70 about its axis so as to properly position port 78, regardless of linear position of piercer 70 pre-fired vs. post-fired (positions discussed later). The slidable interface between probe rotation rod 85 and rod bushing 88 plays an important role in providing this capability.

Probe rotation rod 85 follows the linear movement of piercer 70, while the linear movement of rod bushing 88 is restricted by the fact that it is rotatably attached to top shell 17. Thus the "D" shaped geometry on the proximal end of rotation rod 85 and the "D" shaped hole in the distal end of rod bushing 88, designed to slidably receive the proximal end of rotation rod 85, permit the user to turn port rotation knob 45, which is operably connected to rod bushing 88 through a chain of elements described later, and effect the rotation of piercer 70, irrelevant of the linear position of piercer 70.

Bottom shell 19 fixedly attaches to top shell 17 as described earlier. Its function is to hold in place and contain the elements previously described, which have been assembled into top shell 17. Keyhole 16 is centered at the distal end of bottom shell 19. It slidably and removably engages post 14 (See FIG. 2), permitting probe assembly 42 to be operatively and removably connected to base 44. First screw support rib 111 and second screw support rib 112 are each integrally molded to bottom shell 19 and support the distal and proximal ends, respectively, of elongated screw 114. First gear support rib 136 and second gear support rib 137 likewise are each integrally molded to bottom shell 19 and support the distal and proximal ends, respectively, of elongated drive gear 104. Rod bushing support rib 139 integrally molded to bottom shell 19 supports the distal end of rod bushing 88.

Figure 6:
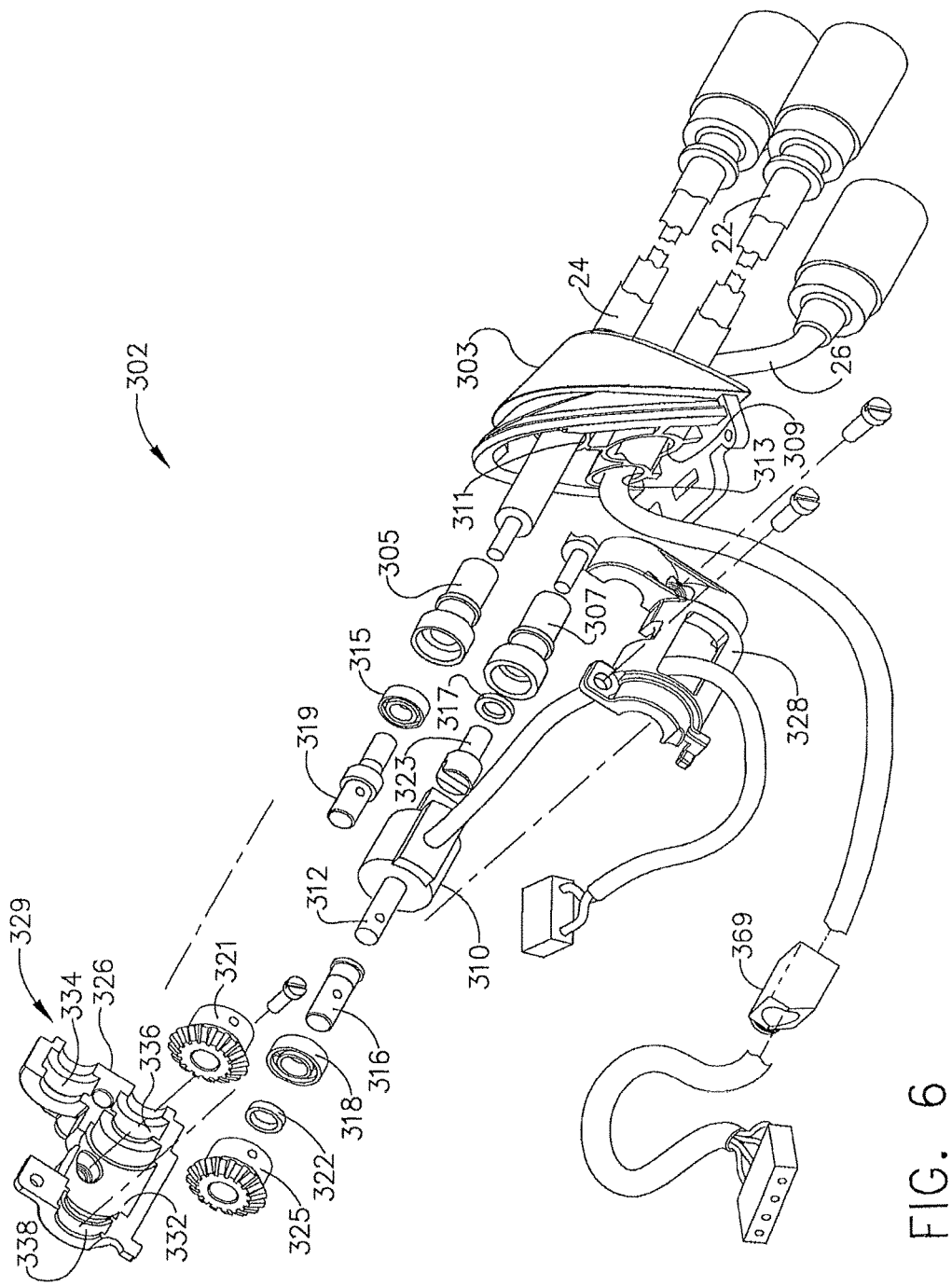
FIG. 6 is an exploded isometric view of the lower transmission assembly of the present invention.

FIG. 6 is an exploded isometric view of lower transmission assembly 302. Translation shaft 22 and rotation shaft 24 is each a flexible coaxial cable comprising a flexible rotatable center core surrounded by a flexible tubular casing, as is well known in the art. At their most proximal ends is provided a coupling means for removably and operatively connecting translation shaft 22 and rotation shaft 24 to control unit 100. The distal ends of translation shaft 22 and rotation shaft 24 each insert through first boot bore 309 and second boot bore 311, respectively. Flex boot 303 is molded from a thermoplastic elastomer such as, for example, polyurethane, and functions as a "flex relief" for translation shaft 22, rotation shaft 24, and control cord 26. Rotation shaft ferrule 305 is a metallic tubular structure comprising a through bore with a counter bore at its proximal end for fixedly attaching, via crimping or swaging as is well known in the art, to the outer tubular casing of rotation shaft 24. At the distal end of rotation shaft ferrule 305 is a flared, counter bored section for receiving first bearing assembly 315. A suitable example of first bearing assembly 315 is Model No. S9912Y-E1531PSO, available from Stock Drive Products, New Hyde Park, N.Y. Rotation shaft adapter 319 is made of stainless steel and has a proximal end with a counter bore. Its proximal end inserts through the bore of first bearing assembly 315 and the counter bore slips over the distal end of the rotatable center core of rotation shaft 24 and is fixedly attached by crimping or swaging. The distal end of rotation shaft adapter 319 is inserted through the bore in first bevel gear 321 and is fixedly attached by a slotted spring pin. Similarly, translation shaft ferrule 307 is a metallic tubular structure comprising a through bore with a counter bore at its proximal end for fixedly attaching, via crimping or swaging, to the outer tubular casing of translation shaft 22. At the distal end of translation shaft ferrule 307 is a flared, counter bored section for receiving thrust washer 317. Translation shaft adapter 323 is made of stainless steel and has a proximal end with a counter bore. Its proximal end inserts through the bore of thrust washer 317 and the counter bore slips over the distal end of the rotatable center core of translation shaft 22 and is fixedly attached by crimping or swaging. The distal end of translation shaft adapter 323 is slotted as a means to engage the proximal end of encoder shaft 312, which extends through encoder 310. Encoder 310 communicates information to control unit 100 about the translation position and translation speed of cutter 96. Encoder 310 includes an electrical cord containing a plurality of electrical conductors, which has an electrical connector affixed at its most distal end for removable electrical connection to printed circuit board 262 (See FIG. 9). A suitable miniature encoder 310 is commercially available as Model sed10-300-eth2 from CUI Stack, Inc. Encoder shaft 312 has two opposing flats on its proximal end, which engage translation shaft adapter 323, and a cylindrical distal end which is inserted into a counter bore in the proximal end of gear adapter 316 and is fixedly attached by a slotted spring pin. The distal end of gear adapter 316 is inserted through the bore of second bearing assembly 318, through the bore of shaft spacer 322, and finally through the bore in second bevel gear 325 which is fixedly attached to gear adapter 316 by a slotted spring pin.

Encoder housing assembly 329 comprises left encoder housing half 326 and right encoder housing half 328, which are molded thermoplastic shells. When assembled, left encoder housing half 326 and right encoder housing half 328 encase encoder 310 and capture the distal end of translation shaft 22 and rotation shaft 24. Left encoder housing half is attached to transmission plate 330 (see FIG. 7) using a cap screw. Encoder 310 is placed in first shell cavity 332, preventing rotational or lateral movement of the outer housing of encoder 310. The distal end of rotation shaft ferrule 305 rests in second shell cavity 334, which prevents lateral movement of rotation shaft 24. The distal end of translation shaft ferrule 307 rests in third shell cavity 336, which again prevents lateral movement of translation shaft 22. Second bearing assembly 318 rests in fourth shell cavity 338. Right encoder housing half 328, containing essentially a minor image of the cavities found inside left encoder housing half 326, assembles to left encoder housing half 326 and transmission plate 330 via two cap screws.

Still referring to FIG. 6, control cord 26 is flexible and contains a plurality of electrical conductors for communication information between biopsy device 40 and control unit 100 (see FIG. 1). At the proximal end of control cord 26 is provided a means of removable electrical connection to control unit 100. The distal end of control cord 26 inserts through third boot bore 313 located in flex boot 303. Control cord strain relief 369 is a flexible thermoplastic material and is over molded to the distal end of control cord 26 and is fixedly attached to transmission plate 330 in a recessed area at strain relief bore 371 (see FIG. 7), to restrict linear and rotational movement of the distal end of the cord. The most distal end of control cord 26 contains a connector for removably and electrically affixing control cord 26 to printed circuit board 262 (see FIG. 9).

Figure 7:
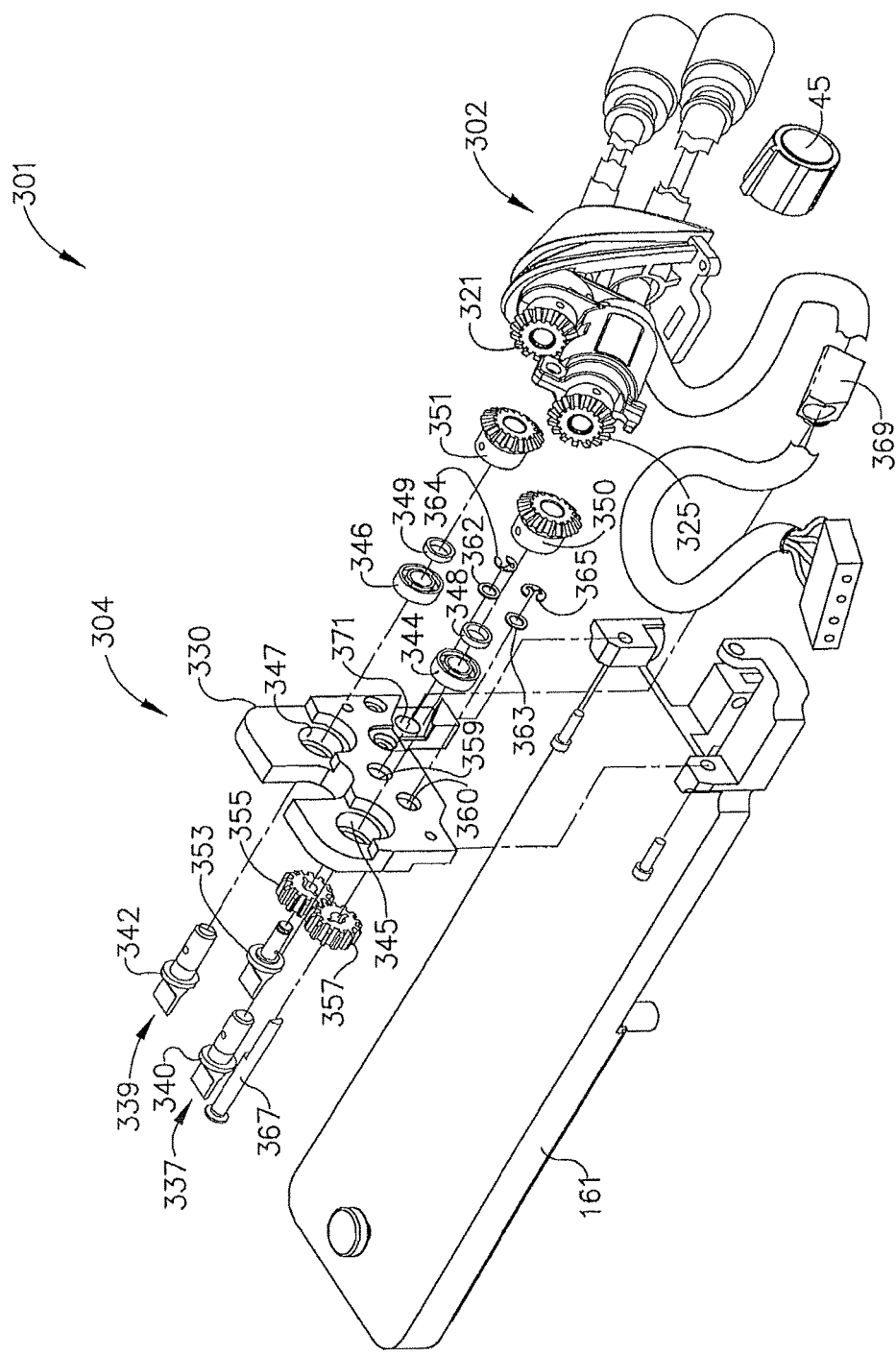
FIG. 7 is an isometric view of the transmission showing the upper transmission assembly exploded.

FIG. 7 is an isometric view of transmission 301. Upper transmission assembly 304 is shown exploded. Translation coupling assembly 337 consists of translation drive coupling 340, third bearing assembly 344, first coupling spacer 348, and third bevel gear 350. Third bearing assembly 344 is press fit into first counter bore 345 in transmission plate 330. Translation drive coupling 340 has a flat bladed distal end which will operatively couple with lead screw slot 122 (see FIG. 8) located at the proximal end of elongated screw 114. The cylindrical proximal end of translation drive coupling 340 inserts through first counter bore 345, through the bore of third bearing assembly 344, through the bore of first coupling spacer 348, and finally through the bore in third bevel gear 350 which is fixedly attached to translation drive coupling 340 by a slotted spring pin. The gear teeth of third bevel gear 350 mesh with the gear teeth of second bevel gear 325. Thus, rotation of the center core of translation shaft 22 results in the rotation of translation drive coupling 340. When translation drive coupling 340 is operatively coupled to elongated screw 114 via lead screw slot 122, rotation of translation shaft 22 causes rotation of elongated screw 114 which results, as discussed earlier, in the distal or proximal translation of cutter 96, depending on the direction of translation shaft 22 rotation.

In a similar manner, rotation coupling assembly 339 consists of rotation drive coupling 342, fourth bearing assembly 346, second coupling spacer 349, and fourth bevel gear 351. Fourth bearing assembly 346 is press fit into second counter bore 347 in transmission plate 330. A suitable example of fourth bearing assembly 346, as well as second and third bearing assemblies 318 and 344, respectively, is available as Model No. S9912Y-E1837PSO, available from Stock Drive Products, New Hyde Park, N.Y. Rotation drive coupling 342 has a flat bladed distal end which will operatively couple with drive gear slot 101 (see FIG. 8) located at the proximal end of elongated drive gear 104. The cylindrical proximal end of rotation drive coupling 342 inserts through second counter bore 347, through the bore of fourth bearing assembly 346, through the bore of second coupling spacer 349, and finally through the bore in fourth bevel gear 351, which is fixedly attached to rotation drive coupling 342 by a slotted spring pin. The gear teeth of fourth bevel gear 351 mesh with the gear teeth of first bevel gear 321. Thus, rotation of the center core of rotation shaft 24 results in the rotation of rotation drive coupling 342. When rotation drive coupling 342 is operatively coupled to elongated drive gear 104 via drive gear slot 101, rotation of rotation shaft 24 causes rotation of elongated drive gear 104, which results in the rotation of cutter 96. A suitable example of first, second, third, and fourth bevel gears 321, 325, 350, and 351, respectively, is Model No. A1M-4-Y32016-M available from Stock Drive Products, New Hyde Park, N.Y.

Continuing in FIG. 7, port drive coupling 353 has a flat bladed distal end which will operatively couple with rod bushing drive slot 91 (see FIG. 8) located at the proximal end of rod bushing 88. The cylindrical proximal end of port drive coupling 353 inserts through the bore in first port gear 355, which is fixedly attached by a slotted spring pin, then inserted through first port coupling bore 359. First coupling washer 362 slips over the proximal end of drive port coupling 353 and first coupling e-ring 364 snaps into a groove at the most proximal end of drive port coupling 353, which now rotatably secures the assembly to transmission plate 330. Knob post 367 is made of stainless steel, is generally cylindrical, and has a flange on its most distal end and a flat approximately one-third to one-half its diameter in depth and extending from its proximal end one half inch in length.

Knob post 367 inserts through the bore of second port gear 357, which is fixedly attached by a slotted spring pin to the distal end of knob post 367. Suitable examples of first and second port gears 355 and 357, respectively, are available as Model No. A1N1-N32012, available from Stock Drive Products, New Hyde Park, N.Y. The proximal end of knob post 367 is inserted through second port coupling bore 360 until second port gear 357 aligns and meshes with first port gear 355. Second coupling washer 363 slips over the proximal end of knob post 367 and second coupling e-ring 365 snaps into a groove located adjacent to the distal end of knob post 367, thus rotatably securing the assembly to transmission plate 330. Port rotation knob 45 fixedly attaches to the proximal end of knob post 367. A suitable port rotation knob 45 is Model No. PT-3-P-S available from Rogan Corp., Northbrook, Ill. Thus, when port drive coupling 353 is operatively coupled to rod bushing 88 via rod bushing drive slot 91, user rotation of port rotation knob 45 causes rotation of rod bushing 88 which results in the rotation of piercer 70. This allows port 78 to be readily positioned anywhere within the 360.degree. axis of rotation of piercer 70.

Transmission plate 330 attaches to the proximal end of upper base shell 161 via two screws.

There is an important benefit derived from the design of transmission 301 just described. The fact that the translation shaft 22, rotation shaft 24, and control cord 26 enter the biopsy device 40 at a right angle to the device's center axis permits for a short overall length for the biopsy device. This allows the device to fit into a smaller area than would accommodate a device with the shafts protruding directly out the back (proximal end) parallel to the center axis.

Figure 8:
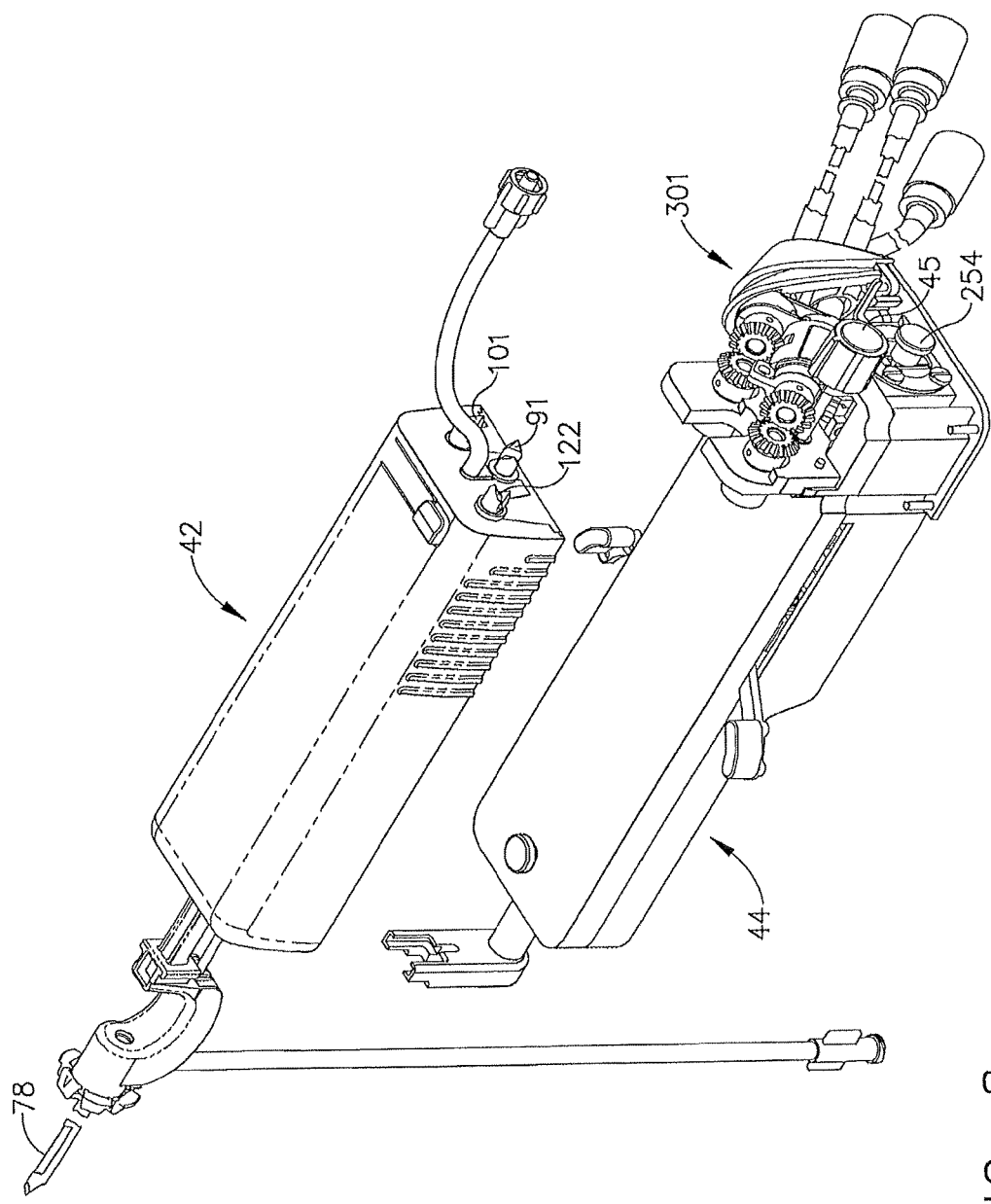
FIG. 8 is an isometric view of the biopsy probe assembly and base assembly, separated, with the upper base housing not shown, as viewed from the proximal end.

FIG. 8 is an isometric view of probe assembly 42 and base 44, as viewed from their proximal ends. Upper base housing 50 is not shown so as to permit a clear view of transmission 301 fully assembled. Also clearly visible are lead screw slot 122, drive gear slot 101, and rod bushing drive slot 91, which operably connect to transmission 301 as previously described.

Figure 9:
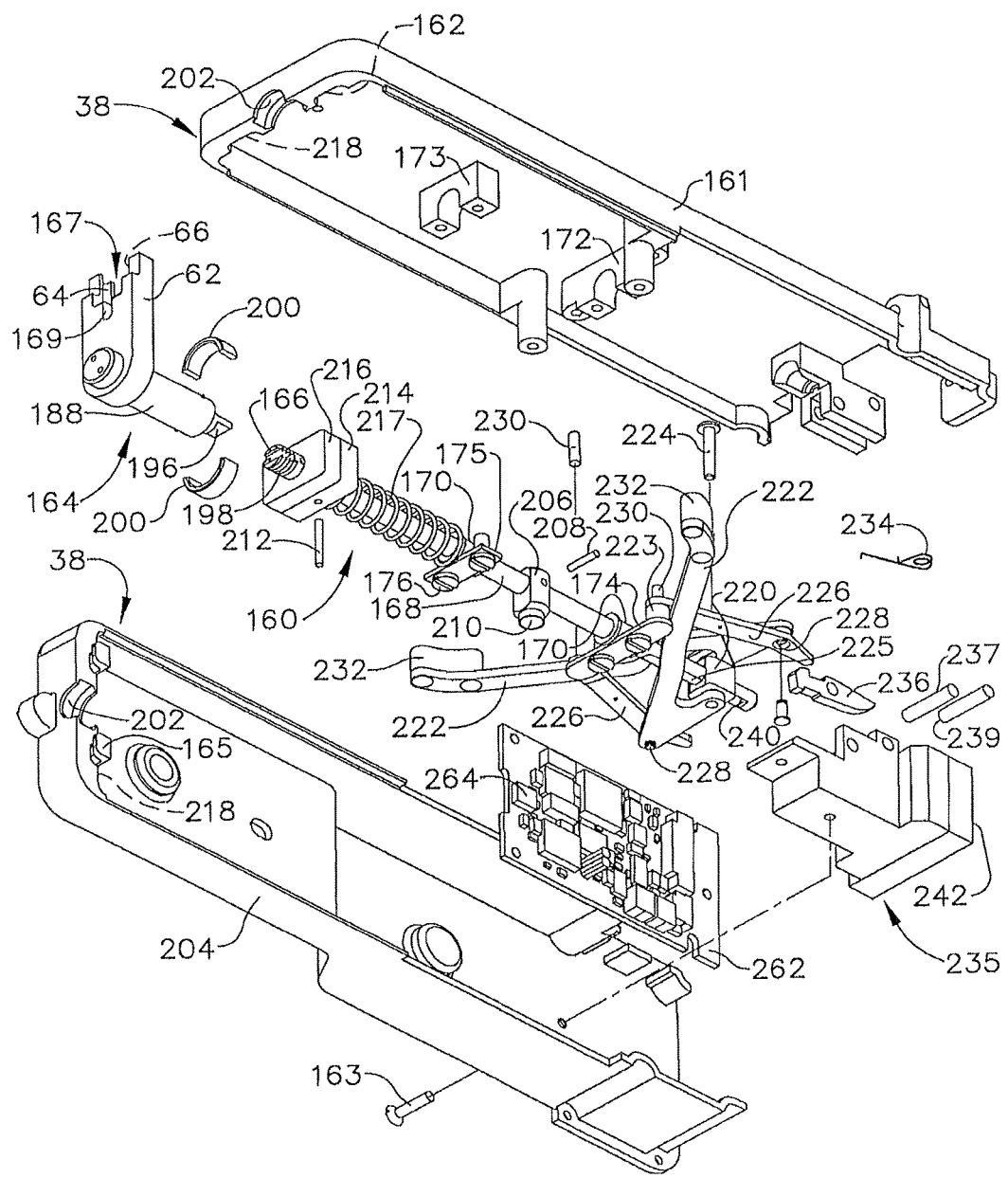
FIG. 9 is an exploded isometric view of the firing mechanism of the present invention.

FIG. 9 is an exploded isometric view of firing mechanism 160. Upper base shell 161 is shown exploded and lower base shell 204 is shown exploded and rotated 90 degrees clockwise. Also exploded and rotated 90 degrees clockwise for clarity is printed circuit board 262 and frame screw 163.

Firing mechanism 160, shown in FIG. 9, operates to fire the distal end of probe assembly 42 into tissue. Base shell 38 (see FIG. 2) supports and houses firing mechanism 160, and is assembled from upper base shell 161 and lower base END-789 shell 204. Base hooks 165 on lower base shell 204 insert into base slots 162 in upper base shell 161 to enable assembly of the components to create base shell 38. Frame screw 163 inserts through a clearance hole in frame bottom 204 and fastens into firing latch block 242 to tie upper base shell 161 and lower base shell 204 together.

Firing fork 62 extends from firing mechanism 160 through to the exterior of base shell 38 to accept probe housing 52 of probe assembly 42 (see FIG. 2). FIG. 9 shows firing fork 62 in its most distal allowable position and shows other components of firing mechanism 160 in appropriate positions for firing fork 62 to be at its most distal allowable position.

Upon mating of the probe assembly 42 with the base 44, first tang 54 and second tang 56 insert into first recess 64 and second recess 66, respectively, in firing fork 62 at the distal end of firing fork assembly 164. Features on firing fork 62 also include probe slot 167, which is approximately "U" shaped to accept probe assembly 42, and clearance slot 169, allowing clearance for probe rotation rod 85.

Figure 10:
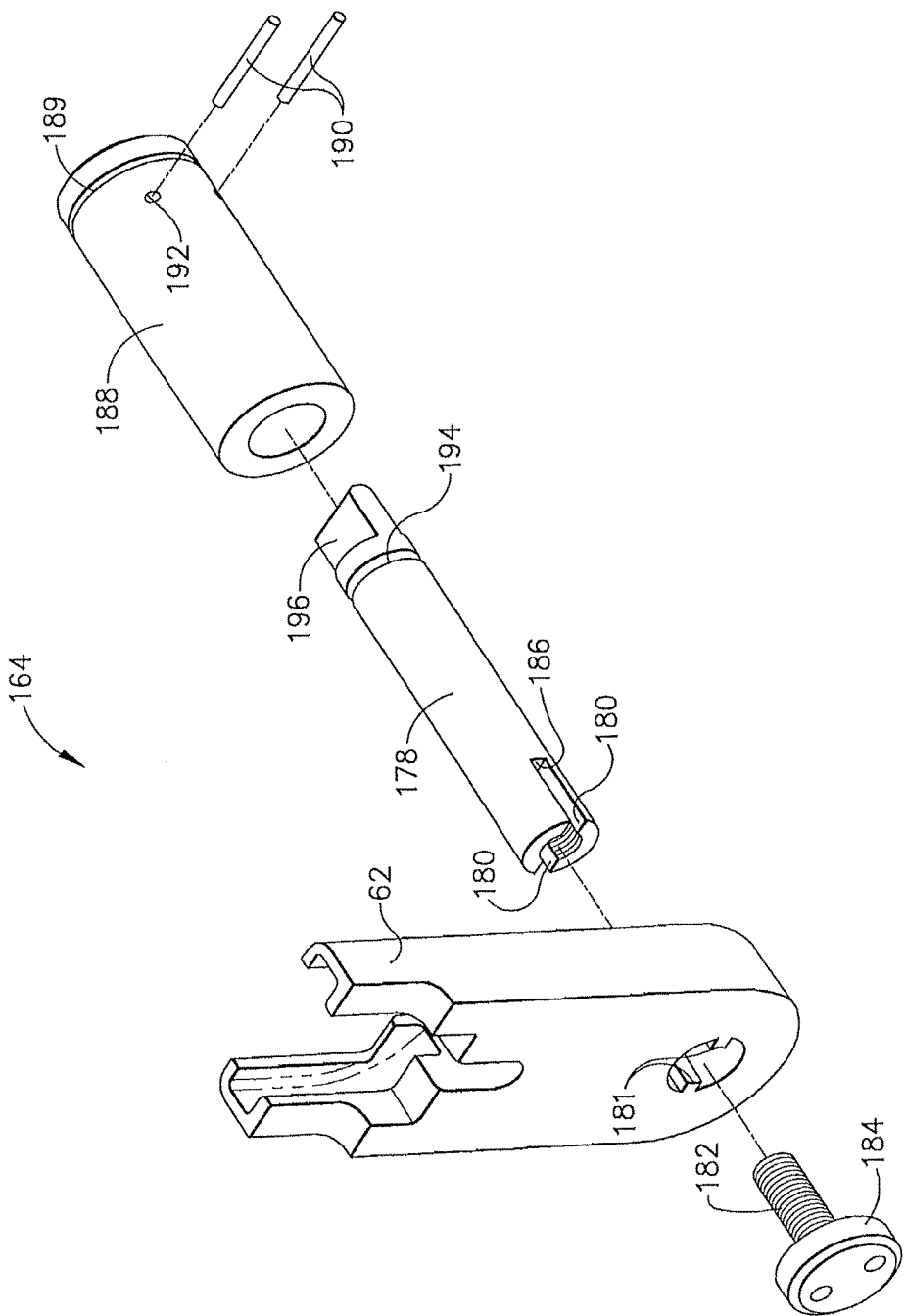
FIG. 10 is an exploded isometric view of an embodiment of the firing fork assembly.

Firing fork assembly 164, shown exploded in FIG. 10, is a unique assembly detachable from the rest of firing mechanism 160 without the use of tools. Firing fork 62 slides over the outer diameter of firing spade 178 while firing fork keys 181 insert into firing spade slots 180. Firing spade slots 180 prevent rotation of firing fork 62 relative to firing spade 178. Firing spade 178 possesses a threaded internal diameter at its distal end and a proximal spade end 196 at its proximal end. Proximal spade end 196 can comprise a flattened section, resembling, for example, the working end of a flathead screwdriver. The threaded diameter at the distal end of firing spade 178 receives screw 182 to hold firing fork 62 to firing spade 178. The head 184 of screw 182 abuts the distal end of firing spade 178 upon tightening. Abutting the head 184 of screw 182 against the distal end of firing spade 178 prevents tightening of the screw against the firing fork 62. The head 184 of screw 182 and the proximal end 186 of firing spade slot 180 provide proximal and distal stops for firing fork 62 while allowing slight axial play.

Firing spacer 188 attaches at the proximal end of firing spade 178 with the aid of dowel pins 190. Firing spacer 188 slips onto and is rotatable relative to firing spade 178. It should be noted that minimizing the clearance between the inside diameter of firing spacer 188 and the outside diameter of firing spade 178 improves the stability of firing fork assembly 164, an important attribute.

Near the proximal end of firing spacer 188, easily visible depth marker line 189 is inscribed. Dowel pins 190 press into receiving holes 192 on firing spacer 188 and ride within firing spade groove 194 to allow rotation of firing spacer 188 relative to firing spade 178 while preventing axial movement of firing spacer 188 relative to firing spade 178. A threaded internal diameter at the proximal end of firing spacer 188 facilitates assembly and removal of the firing fork assembly 164 for cleaning.

FIG. 9 shows that firing fork assembly 164 threads onto end fitting 166, pinned at the distal end of firing fork shaft 168. End fitting 166 can be made of a soft stainless steel for easy machining of slot and threads while firing fork shaft 168 can be made of a hardenable stainless to accommodate induced stress. Proximal spade end 196 fits into spade slot 198 of end fitting 166 to prevent rotation of firing fork assembly 164 relative to firing fork shaft 168. The threaded internal diameter of the proximal end of firing spacer 188 screws onto the threaded outer diameter of end fitting 166 to removably attach firing fork assembly 164. Small firing bushings 170, fashioned from a plastic such as acetal, support firing fork shaft 168 and allow it to move proximally and distally. Proximal saddle support 172 and distal saddle support 173, machined into upper base shell 161, support small firing bushings 170 while long clamp plate 174 and short clamp plate 175 capture and retain small firing bushings 170 into proximal and distal saddle supports 172 and 173, respectively. Long clamp plate 174 and short clamp plate 175 can attach to proximal saddle support 172 and distal saddle support 173 using fasteners, such as, for example, clamp plate mounting screws 176. Flanges at each end of the small firing bushings 170 bear against the proximal and distal sides of saddle supports 172 and clamp plates 174 to restrain small firing bushings 170 from moving proximally and distally with the movement of firing fork shaft 168. Additional support is gained by the large firing bushing 200 surrounding firing spacer 188. Large firing bushing 200, split for easy assembly, resides in firing bushing housing 202 machined into upper base shell 161 and lower base shell 204.

Firing fork shaft 168 carries other parts that facilitate the operation of firing mechanism 160. Spring collar roll pin 212 fixedly attaches spring collar 214 to firing fork shaft 168. Shock pad 216 adheres to the distal side of spring collar 214 and contacts distal interior wall 218 of base shell 38 when firing fork shaft 168 is in its distal position. Shock pad 216 can be made from many shock-absorbing materials, such as, for example, rubber. Main spring 217 surrounds firing fork shaft 168 and bears against the distal side of distal saddle support 173 and the proximal side of spring collar 214 to force firing fork shaft 168 distally. Magnet holder roll pin 208 fixedly attaches magnet holder 206 to firing fork shaft 168. Magnet 210 is crimped into magnet holder 206. Nearer the proximal end of firing fork shaft 168, firing main link pin 224 passes through firing fork shaft slot 225 to hold firing fork shaft 168 to carriage 220. Firing main link pin 224 also captures curved firing levers 222 retaining them to the carriage 220. Firing main link pin 224 is flanged on one end. The other end of firing main link pin 224 extends through carriage 220 to retain carriage 220, firing fork shaft 168, and curved firing levers 222, where it is retained by welding to the lower curved firing lever.

Curved firing levers 222 and firing linkages 226 drive the arming of firing mechanism 160. Curved firing levers 222 pin to firing linkages 226 using firing link pins 228 which are welded to firing levers 222. Firing linkages 226 in turn pin to upper base shell 161 using frame link dowel pins 230 pressed into upper base shell 161. Long clamp plate 174 retains firing linkages 226 using clamp plate mounting screws 176. Each pinned joint of curved firing levers 222, firing linkages 226, and carriage 220 is rotatably movable about the axis of the pin.

Each curved firing lever 222 has a portion that extends laterally outwards through a slot located on either side of base shell 38 (See FIG. 2). A curved firing lever end 232 is attached to each curved firing lever 222 on the extension of curved firing lever 222 external to base shell 38. Curved firing lever end 232 provides a convenient user interface for arming the firing mechanism. Arming the mechanism will be described later. The coil of torsion spring 234 surrounds each pinned joint of curved firing levers 222 and firing linkages 226. The legs of link torsion springs 234 extend outwardly to hook into curved firing levers 222 and firing linkages 226, applying a torque rotating them relative to each other.

Locating firing linkages 226 and curved firing levers 222 at different distances from upper base shell 161 allows them clearance to pass by each other upon operation. Curved firing levers 222 have bends to offset them in a direction perpendicular to upper base shell 161. The offset bends let them move within planes at different distances from upper base shell 161 while having the curved firing lever ends emerge from the slot created for that purpose in upper base shell 161. Spacer 223 separates the links on the pin 230. Having a curved firing lever 222 and firing linkage 226 on each side of the longitudinal centerline allows access by the user to operate firing mechanism 160 from either side of base shell 38.

Fasteners secure a printed circuit board 262 to lower base shell 204 and latch block 242. Printed circuit board 262 contains Hall-effect switch 264 for sensing the proximity of magnet 210. A suitable Hall-effect switch 264 is Model No. A3142ELT available from Allegro Microsystems, Inc., Worcester, Mass. When firing fork 168 and associated magnet 210 are in the most proximal position (pre-fired position, as described later), magnet 210 is held in a position near Hall-effect switch 264.

Figure 11:
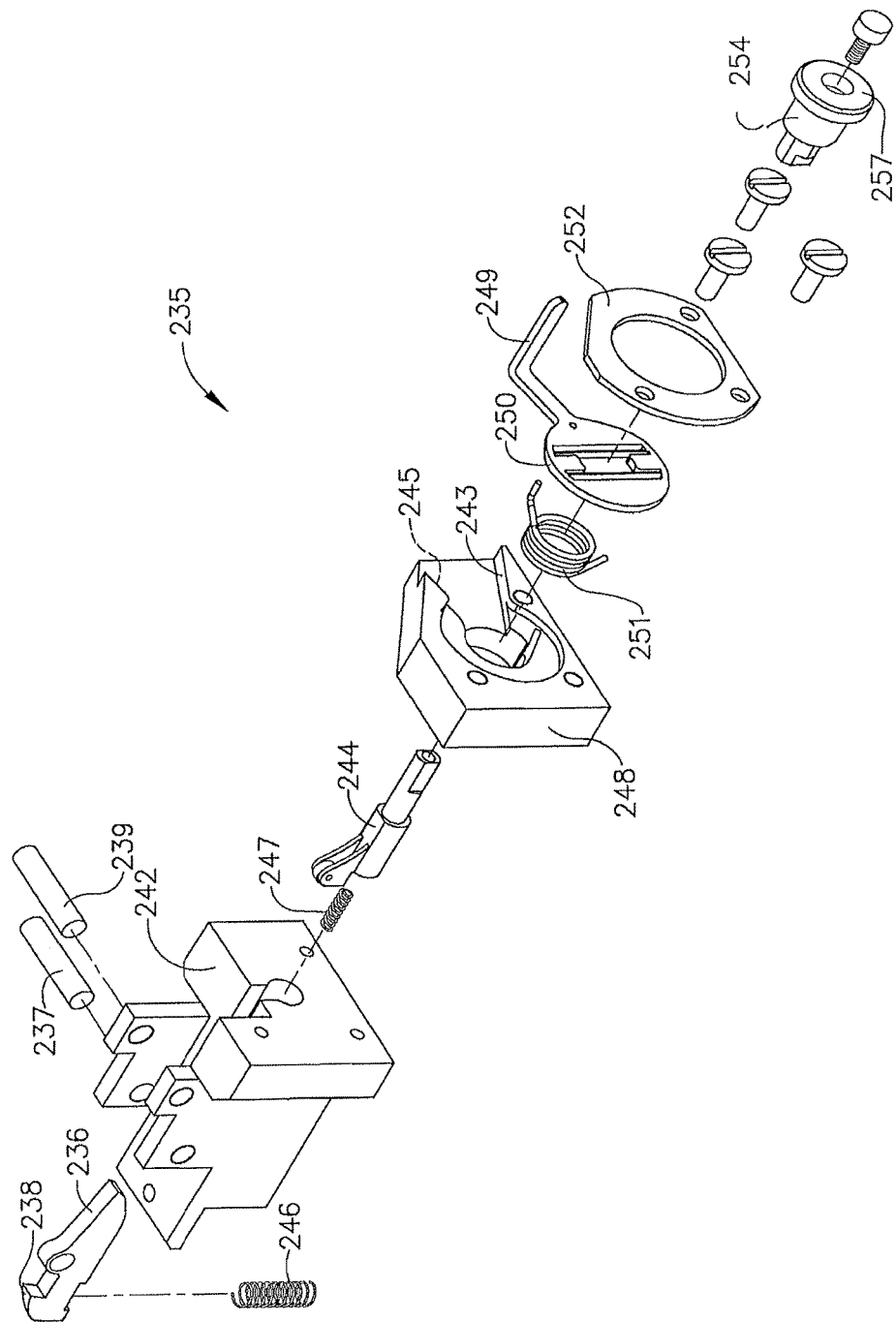
FIG. 11 is an exploded isometric view of the triggering mechanism of the present invention.

FIG. 11 is an exploded isometric view of triggering mechanism 235, seen in FIG. 9. Triggering mechanism 235 safely latches and fires firing fork shaft 168. Triggering mechanism 235 comprises firing latch 236, firing latch block 242, firing button shaft 244 and roller 241, firing latch spring 246, firing button shaft spring 247, safety block 248, safety latch 250, safety latch torsion spring 251, safety latch cover 252, and firing button 254.

Firing latch block 242 encloses the proximal portion of firing latch 236 and serves as a mounting platform for components of triggering mechanism 235, Firing latch pin 237 and firing block pin 239 rigidly retain firing latch block 242 to upper base shell 161. Firing latch pin 237 rotatably pins firing latch 236 to upper base shell 161 while passing through firing latch block 242. Firing latch 236 pivots within a slot in upper base shell 161. Firing latch spring 246 is compressed between firing latch block 242 and firing latch 236, thereby forcing the distal end of firing latch 236 towards firing fork shaft 168. Firing latch 236 possesses a firing latch hook 238 at its distal end, which removably latches into a firing fork shaft retainer 240 located at the proximal end of firing fork shaft 168. Firing button shaft 244 slidably moves proximally and distally within a bore in firing latch block 242 and has roller 241 rotatably pinned to its distal portion to engage firing latch 236 to cause rotation of firing latch 236. Firing button shaft spring 247 forces firing button shaft 244 proximally. Firing button shaft 244 is retained by safety block 248, which is mounted to the proximal side of firing latch block 242. Safety latch 250 resides within a counter bore on the proximal side of safety block 248 and is retained by safety latch cover 252. Fasteners such as screws hold safety latch cover 252 in place.

Safety latch 250 is designed to facilitate locking and unlocking of the firing mechanism. Safety latch 250 can be rotated within the counter bore on safety block 248 through a rotation angle, while safety latch torsion spring 251 has extending legs hooked into safety block 248 and safety latch 250 to apply torque to safety latch 250. Safety block 248 defines a locked position safety latch stop 245 and an unlocked position safety latch stop 243 separated by the rotation angle.

Figure 12:
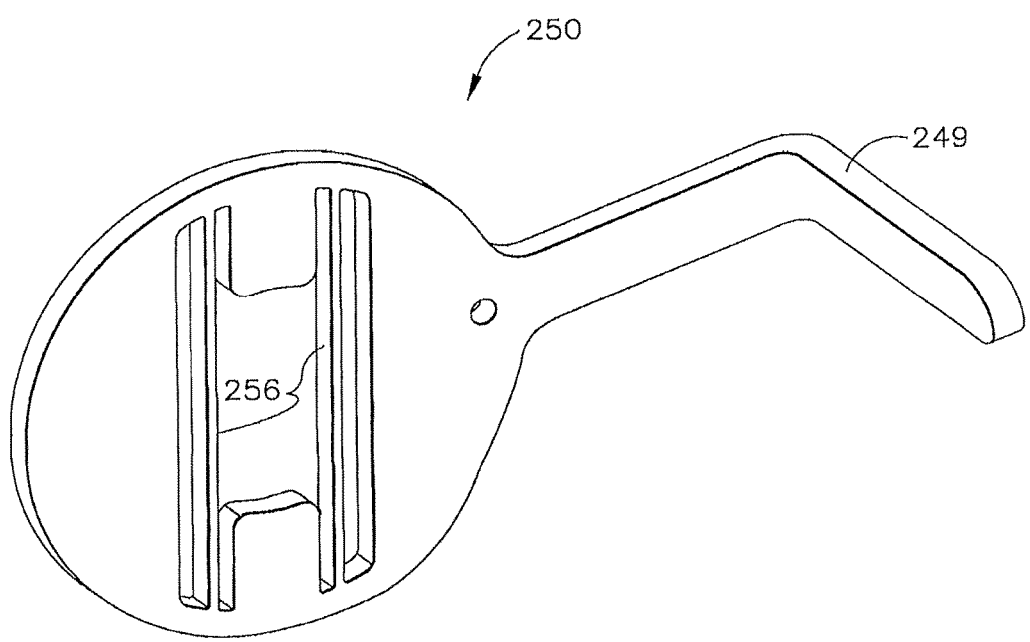
FIG. 12 is an isometric view of the safety latch.

Safety latch handle 249 extends radially from safety latch 250 to facilitate grasping and rotating of safety latch 250 by the user. Safety latch handle 249 also forms surfaces to abut safety latch stops 245 and 243 to limit the rotation angle. In the locked position, safety latch torsion spring 251 forces safety latch handle 249 against the locked position safety latch stop 245, while in the unlocked position, the user forces safety latch handle 249 against unlocked position safety latch stop 243. In the illustrated embodiment of the invention, the rotation angle through which safety latch 250 can be rotated is about thirty-five degrees. FIG. 12 shows that safety latch 250 contains two firing button stops 256 with one firing button stop 256 on each side of the longitudinal axis of firing button 254 at assembly. The firing button stops 256 interact with firing button 254 to effect locking (preventing lateral movement) and unlocking (allowing lateral movement) of firing button 254.

Figure 13:
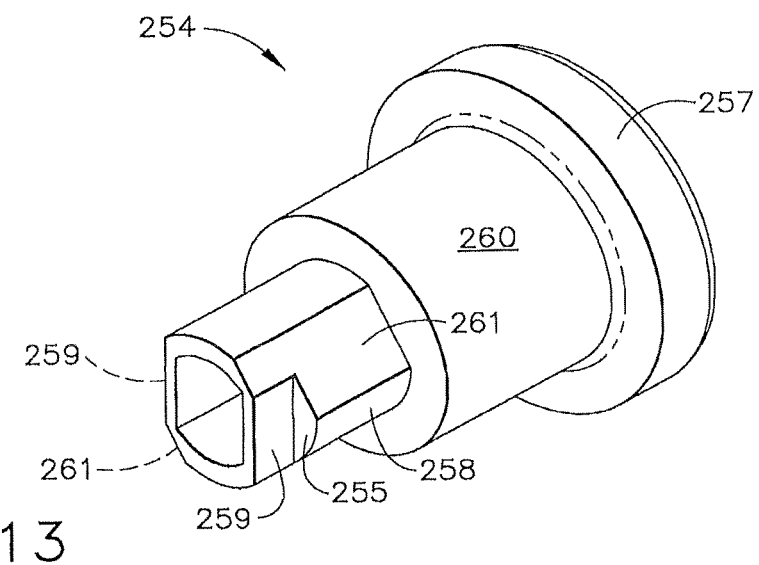
FIG. 13 is an isometric view of the safety button.

FIG. 13 shows an isometric view of firing button 254. Firing button 254 fixedly attaches to firing button shaft 244 (see FIG. 11), extends proximally through the center of safety latch 250 (see FIG. 12), and presents a proximal, flattened, cylindrical thumb pad 257 located at its most proximal end to the user.

Firing button 254 comprises a smaller firing button outer diameter 258 having narrow flats 259 and wide flats 261 angularly offset from each other by the rotation angle traveled by safety latch 250. Larger firing button outer diameter 260 is free of flats. A distal contact surface 255 exists proximally of narrow flats 259 and is substantially perpendicular to the longitudinal axis of firing button 254. Firing button stops 256, located on safety latch 250, are separated by a distance slightly larger than the distance between wide flats 261 and less than the smaller firing button outer diameter 258. Firing button stops 256 can flex in the radial direction, but resist flexing in the axial direction. The difference in stiffness in different directions can be accomplished by, for example, different thicknesses of the firing button stops 256 in the axial direction and in the radial direction.

When safety latch 250 is in the locked position, pushing firing button 254 will force distal contact surface 255 against firing button stops 256. Firing button stops 256 prevent further proximal axial movement of firing button 254 because of rigidity in the axial direction.

Following is a functional description of the operation of the firing mechanism of the present invention:

A user arms and fires the firing mechanism during use of the probe assembly 42 in a surgical procedure. The user begins in the fired position depicted in FIGS. 14 and 15, grasps one of the curved firing lever ends 232, and moves outboard end of curved firing lever 222 proximally. This begins action wherein each grasped curved firing lever 222, each firing linkage 226, carriage 220, and upper base shell 161 act as four-bar linkage systems with upper base shell 161 being the stationary link and carriage 220 being a translational link. Motion can be described of all three movable links relative to the upper base shell 161. Either curved firing lever end 232 can be moved by the user. Duplicity exists in the illustrated embodiment of the invention to facilitate user access from either side of base 44.

Rotating either curved firing lever 222 in a direction that moves the curved firing lever end 232 proximally effects motion of the two members pinned to curved firing member 222. Curved firing member 222 transfers motion through one pinned joint to carriage 220 to move it proximally along firing fork shaft 168. Curved firing member 222 also transfers motion through a second pinned joint to firing linkage 226, rotating the pinned joint towards firing fork shaft 168. Firing linkage 226 is pinned to stationary upper base shell 161 and rotates about the pinned joint located on upper base shell 161.

Carriage 220, driven by curved firing member 222, translates proximally along firing fork shaft 168 carrying main link pin 224 within firing fork shaft slot 225 until firing main link pin 224 reaches the proximal end of firing fork shaft slot 225. Further proximal motion of carriage 220 and firing main link pin 224 begins to drive proximal motion of firing fork shaft 168. Firing fork shaft 168 translates proximally through small firing bushings 170.

Figure 16:
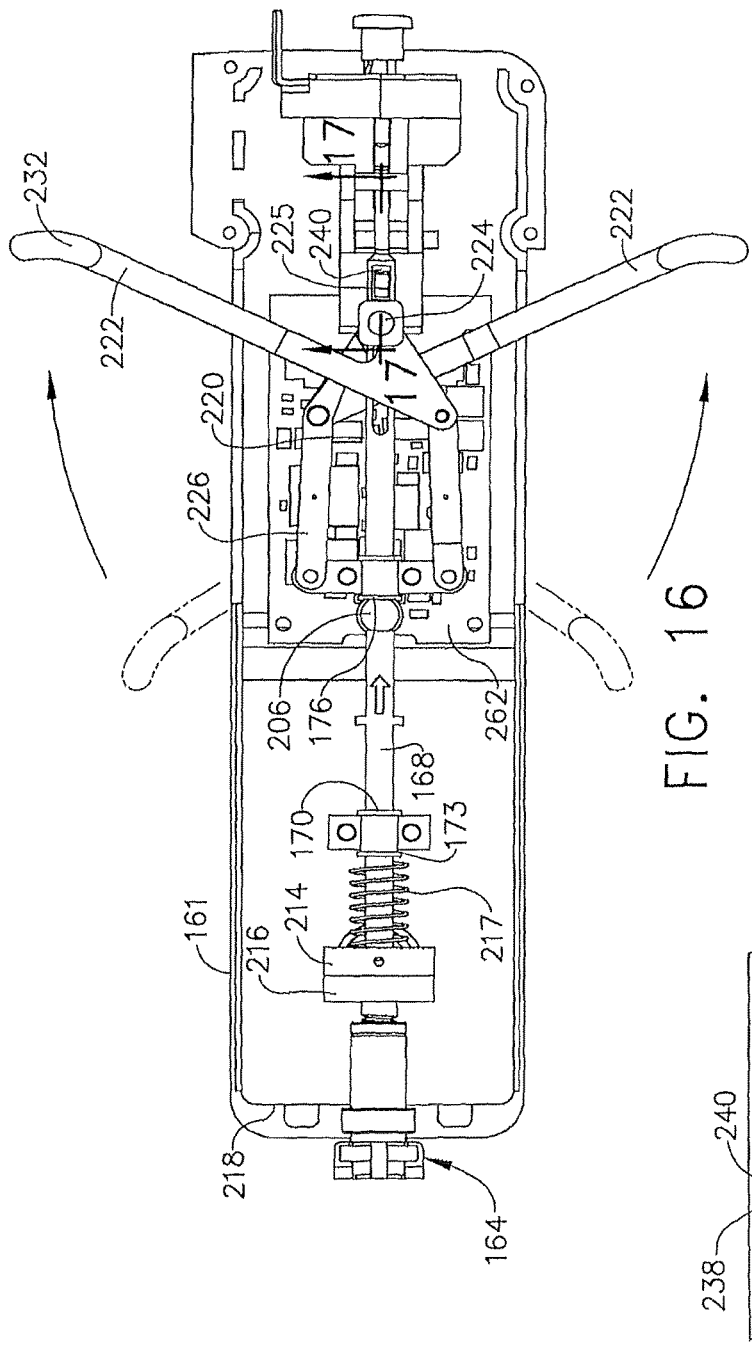
FIG. 16 is a top view of the firing mechanism of the present invention showing the mechanism in the pre-fired position.
Figure 17:
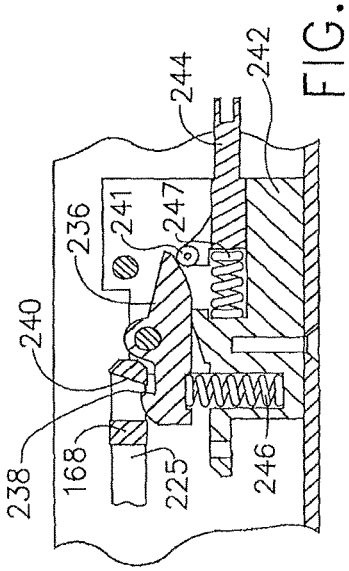
FIG. 17 is a partial, plan sectional view of the firing mechanism in the pre-fired position showing the firing latch and firing rod.

As firing fork shaft 168 translates proximally, it carries with it attached firing fork assembly 164. Firing fork shaft 168 also carries proximally attached spring collar 214, decreasing the distance between spring collar 214 and distal saddle support 173. Main spring 217, located between spring collar 214 and distal saddle support 173, becomes more compressed exerting more force against spring collar 214. Firing fork shaft 168 continues to move proximally and continues to compress main spring 217 until the proximal end of firing fork shaft 168 reaches firing latch 236 (see FIG. 15). The proximal end of firing fork shaft 168 contacts firing latch 236 and exerts a force rotating it out of the path of proximally advancing firing fork shaft 168. The proximal end of firing fork shaft 168 and the distal end of firing latch 236 have contoured surfaces to act as cams to assist in lifting firing latch 236. Rotating firing latch 236 compresses firing latch spring 246, exerting a force to hold firing latch 236 onto the proximal end of firing fork shaft 168. Once the firing fork shaft retainer 240 has proceeded proximally to a position under firing latch hook 238, firing latch spring 246 urges firing latch hook 238 into firing fork shaft retainer 240 by rotating firing latch 236 towards firing fork 168. Firing assembly 160 is now in the pre-fire position shown in FIGS. 16 and 17.

The user can now release curved firing lever end 232. Once the user releases curved firing lever end 232, main spring 217 applies force urging firing fork 168 distally along its axis. The distal force moves firing fork shaft retainer 240 towards firing latch hook 238 extending down into firing fork shaft retainer 240 (see FIG. 19). The proximal wall of firing fork shaft retainer 240 is angled so that the reactive force of the proximal wall of firing fork shaft retainer 240 against firing latch hook 238 rotates firing latch hook 238 further into the firing fork shaft retainer 240, preventing inadvertent release. The proximal wall of firing latch hook 238 is angled to mate with the angle of the proximal wall of firing fork shaft retainer 240. After the user has released curved firing lever end 232, link torsion springs 234 apply torque to curved firing levers 222 and firing linkages 226 rotating them towards each other. Rotating curved firing levers 222 and firing linkages 226 towards each other initiates motion that returns carriage 220 to its distal position. With firing fork 168 held by firing latch 236 while firing levers 222 and firing linkages 226 are in the most distal position, firing mechanism 160 is in the relaxed position shown in FIGS. 18 and 19. When carriage 220 returns to its distal position, curved firing levers 222 contact stops on the sides of raised bosses on upper base shell 161.

Firing fork shaft 168 has now carried magnet 210 (see FIG. 9) which is located within magnet holder 206 proximally into a position near Hall-effect switch 264 on printed circuit board 262. Hall-effect switch 264 senses the presence of magnet 210 and communicates with control unit 100 that firing fork 168 is in a proximal position and ready to fire.

Figure 20:
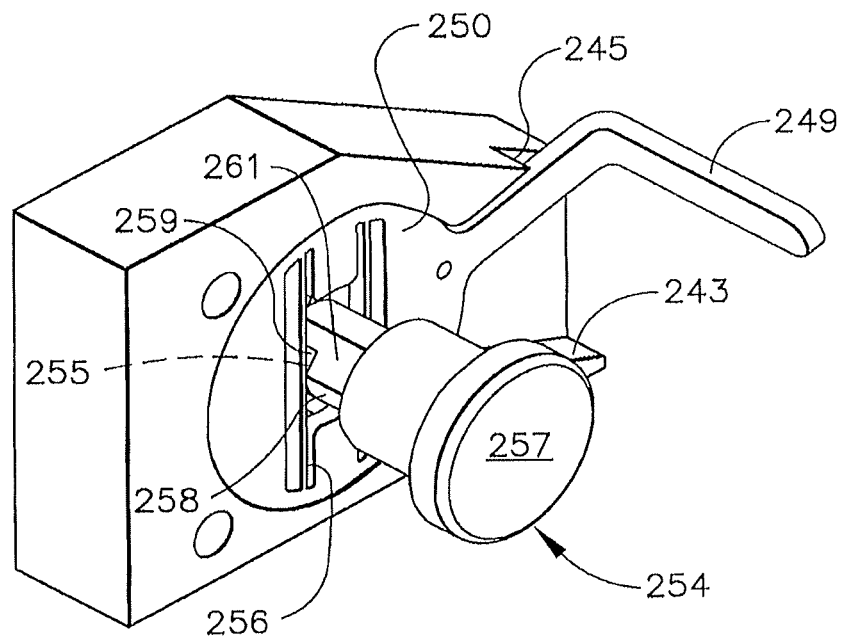
FIG. 20 is an isometric view of the safety latch and safety button shown in the locked position.

Safety latch 250 "guards" firing button 254. In the locked position shown in FIG. 20, firing button stops 256 on the safety latch 250 are located distally of distal contact surface 255 on firing button 254. Firing button stops 256 on safety latch 250 are also located on either side of narrow flats 259 (see FIG. 13). Smaller firing button outer diameter 258 is larger than the distance between firing button stops 256. Attempting to push firing button 254 distally will cause distal contact surface 255 to contact firing button stops 256. The rigidity of the firing button stops 256 in the axial direction prevents further distal movement of the firing button and prevents inadvertent firing of the mechanism.

Figure 21:
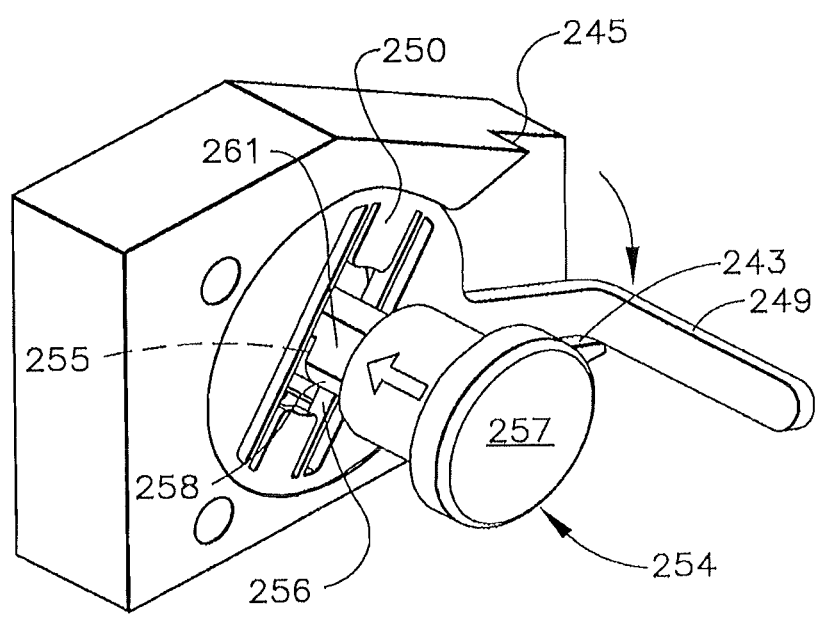
FIG. 21 is an isometric view of the safety latch and safety button shown in the firing position.

After the user has determined the proper location in which to insert the piercer 70 of biopsy device 40 into a surgical patient, the user can now unlock and fire firing mechanism 160. Unlocking and firing the mechanism requires two separate actions, rotating the safety latch 250 and pressing the firing button 254. The operator first grasps safety latch handle 249 to rotate safety latch 250 against the torque applied to it by safety latch torsion spring 251 (not visible). FIG. 21 shows rotating safety latch 250 so that safety latch handle 249 travels from locked position safety latch stop 245 to unlocked position safety latch stop 243 which aligns firing button stops 256 with wide flats 261 on smaller firing button outer diameter 258. Since the distance between firing button stops 256 is larger than the distance between wide flats 261, clearance now exists for wide flats 261 to pass between firing button stops 256. Safety latch 250 is now in the "firing" position.

In the next step, the operator presses firing button 254 by placing force on cylindrical thumb pad 257 to urge firing button 254 distally. When firing button 254 is pressed, wide flats 261 move between firing button stops 256 allowing firing button 254 to proceed distally. Firing button 254, attached to firing button shaft 244, pushes firing button shaft 244 distally. The roller 241 on firing button shaft 244 contacts the cam surface on firing latch 236 to rotate firing latch 236 so that firing latch hook 238 lifts out of firing fork shaft retainer 240 (see FIG. 19).

Once firing latch hook 238 is clear of firing fork shaft retainer 240, main spring 217 drives firing fork shaft 168 distally carrying firing fork assembly 164 and piercer 70 of probe assembly 42 towards the target. Distal motion of firing fork shaft 168 continues until shock pad 216 contacts distal interior wall 218 of base shell 38 (see FIG. 14). Hall-effect switch 264 senses the departure of magnet 210 distally and communicates the departure to control unit 100.

After firing the firing mechanism 160 the user releases firing button 254, then releases safety latch handle 249. When the user releases firing button 254, firing button shaft spring 247 forces firing button shaft 244 proximally. Firing button 254 moves proximally as well, returning distal contact surface 255 and firing button smaller diameter 258 proximal of firing button stops 256. The proximal movement of firing button 254 also places narrow flats 259 between firing button stops 256. Releasing safety latch handle 249 allows safety latch torsion spring 251 to rotate safety latch 250 back towards the locked position with safety latch handle 249 forced against locked position safety latch stop 245. With only narrow flats 259 and wide flats 261 between firing button stops 256, safety latch 250 can freely rotate without interference from firing button stops 256.

When firing button shaft 244 travels proximally, the roller 241 of firing button shaft 244 and cammed surface of firing latch 236 separate (see FIG. 15). Firing latch spring 246 then rotates firing latch 236 into a position where firing latch hook 238 is moved towards firing fork shaft 168. An arming and firing cycle is now complete. Firing assembly 160 has returned to the post-fired position depicted in FIGS. 14 and 15.

It should be noted that if, after firing, the user of the firing mechanism 160 does not release firing button 254 before releasing safety latch handle 249, the mechanism still operates properly because of incorporated unique design features. When firing button 254 is in the distal, pressed position, smaller firing button outer diameter 258 is between firing button stops 256. Clearance for firing button stops 256 is made by alignment of firing button stops 256 with wide flats 261. Releasing safety latch handle 249 before releasing firing button 254 causes safety latch torsion spring 251 to rotate safety latch 250 back towards the locked position and causes firing button stops 256 to rotate out of alignment with wide flats 261. When the firing button stops 256 rotate out of alignment with wide flats 261 smaller firing button outer diameter 258 comes between firing button stops 256. Smaller firing button outer diameter 258 is larger than the distance between firing button stops 256. However, firing button stops 256, designed to flex in the radial direction, separate by bending away from each other in the center when forced apart by smaller firing button outer diameter 258. Because of the radial flexibility of firing stops 256, firing button stops 256 apply little force to smaller firing button outer diameter 258. With little force applied, firing button 254 slides easily through firing button stops 256 while returning to the proximal position. Firing button 254 returning to its proximal position brings smaller firing button outer diameter 258 between firing button stops 256 to allow safety latch 250 to continue to rotate back to the locked position. The difference in flexibility of the firing button stops radially and axially allows latching and release of triggering mechanism 235 regardless of order of operation of the components. Rigidity in the axial direction stops inadvertent operation of firing button 254 and flexibility in the radial direction allows interference with smaller firing button outer diameter 258 while still maintaining smooth release operation.

If desired, firing fork assembly 164 can be disassembled without tools from the rest of firing mechanism 160 and cleaned. Before a subsequent firing, an operator can attach a clean firing fork assembly 164 by mating proximal spade end 196 with spade slot 198 and threading firing spacer 188 onto end fitting 166. When assembling firing fork assembly 164 with the firing mechanism in the post-fired position, an assembler can use depth marker line 189 to ensure proper assembly. The assembler can check alignment of depth marker line 189 with the outside surface of base shell 38. A depth marker line 189 aligned with base shell 38 denotes a proper assembly. A depth marker line 189 that is misaligned with base shell 38 could indicate an improper assembly such as cross threading of firing spacer 188 or incomplete tightening of firing spacer 188.

Figure 22:
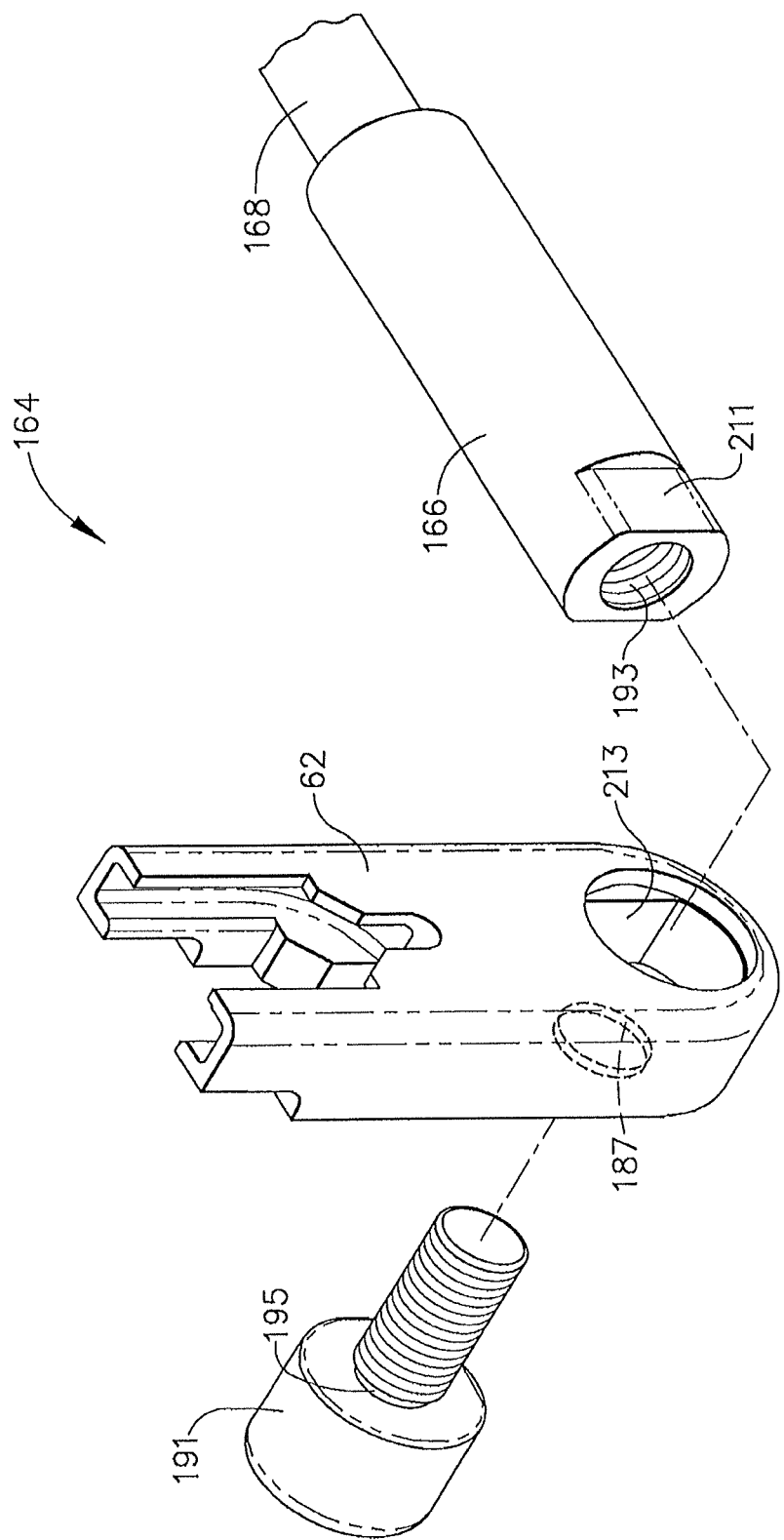
FIG. 22 is an exploded isometric view of an alternate embodiment of the firing fork assembly.

FIG. 22 shows an alternate embodiment of firing fork assembly 164. Thumbscrew 191 threads into a threaded hole 187 on firing fork 62. Threaded hole 187 on firing fork 62 passes through to a larger counter bore hole with flats on either side, commonly called a double-D hole 213. Firing fork assembly 164 comprises thumbscrew 191 threaded onto firing fork 62. Undercut 195 has an outer diameter less than the minor diameter of threaded hole 187 on firing fork 62 and thus maintains clearance between threaded hole 187 and undercut 195. Thumbscrew 191, after assembly to firing fork 62, can thus turn freely on firing fork 62 utilizing the clearance between threaded hole 187 and undercut 195. An alternate embodiment of firing fork shaft end fitting 166, shown in FIG. 22, has end fitting flats 211 machined on either side of the second embodiment of end fitting 166. End fitting 166 is welded to the distal end of firing fork shaft 168. The configuration of end fitting 166 with end fitting flats 211 will accept double-D hole 213 of the alternate embodiment of firing fork 62. Use of end fitting flats 211 with double-d hole 213 prevents rotation of firing fork 62 relative to end fitting 166 and firing fork shaft 168. The alternate embodiment of firing fork assembly 164 threads into alternate embodiment of end fitting 166 which is welded onto firing fork shaft 168. The alternate embodiment end fitting 166 has a threaded internal diameter 193 to accept the threaded proximal end of thumbscrew 191. Thumbscrew 191 has a knurled, easily grasped surface so that the alternate embodiment of firing fork assembly 164 can be assembled and disassembled without the use of tools.

Dual four-bar mechanisms have been utilized in the present embodiment of the invention to facilitate ease of use by providing access by the user from either side of base 44. A variation that would become evident to one skilled in the art after reading the description would be a single four-bar mechanism to create the firing mechanism.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A biopsy device, comprising:
(a) a reusable portion, including a housing;
(b) a disposable probe portion including a housing removably coupled to the housing of the reusable portion, wherein the probe portion includes a needle extending distally from the housing of the probe portion;
(c) a cutter movable with respect to an opening in the needle to sever a tissue sample received in the opening in the needle;
(d) a firing assembly operable to distally advance the needle of the probe portion, wherein the firing assembly includes:
(i) a loading assembly,
(ii) a release assembly, and
(iii) a spring,
wherein the loading assembly is configured to drive at least a portion of the spring proximally to load the spring, wherein the release assembly includes a rotatable cam lock, wherein the loading assembly is configured to release the spring to drive the needle distally in response to movement of the rotatable cam lock;
(e) a vacuum source, wherein the vacuum source is operable to communicate vacuum through the cutter;

(f) a first cutter motion assembly, wherein at least a portion of the first cutter motion assembly is located within the housing of the probe portion, wherein the first cutter motion assembly includes a lead screw and a carriage assembly, wherein the carriage assembly is configured to move the cutter axially in response to rotation of the lead screw;

(g) a second cutter motion assembly, wherein the second cutter motion assembly includes an elongate spur gear including a plurality of elongate teeth, wherein the second cutter motion assembly is operable to communicate motion to the first cutter motion assembly via the elongate spur gear, wherein the second cutter motion assembly is configured to communicate rotational motion to the first cutter motion assembly to thereby rotate the cutter as the cutter is moved axially by the carriage.

2. The biopsy device of claim 1, further comprising a first fluid line and a second fluid line, wherein the needle includes a first lumen and a second lumen.

3. The biopsy device of claim 2 further comprising a plurality of openings between the first lumen and the second lumen.

4. The biopsy device of claim 2 wherein the first fluid line communicates with the first lumen.

5. The biopsy device of claim 2, wherein the second fluid line communicates with the second lumen.

6. The biopsy device of claim 1 wherein the biopsy device includes a tissue remover, and wherein a strainer is disposed on an end of the tissue remover.

7. The biopsy device of claim 1 wherein the needle is rotatable with respect to the reusable portion.

8. The biopsy device of claim 1 wherein the needle is rotatable with respect to the firing assembly.

9. A biopsy device, comprising:
(a) a body, wherein the body is defined by a holster housing and a probe housing;
(b) a needle extending distally from the probe housing of the body, the needle having a tissue receiving opening;
(c) a cutter moveable relative to the tissue receiving opening in the needle;
(d) a firing assembly operable to fire the needle into tissue, wherein the firing assembly includes:
(i) a firing rod,
(ii) an actuator, and
(iii) a coil spring,
wherein the firing rod is configured to translate proximally to compress the coil spring, wherein the firing rod is further configured to translate distally to fire the needle distally relative to the body in response to movement of a cam surface of the actuator relative to the firing rod;
(e) a strainer operable to permit fluid to pass through the strainer, and the strainer operable to prevent a tissue sample from passing through the strainer;
(f) a vacuum source, wherein the vacuum source is operable to provide vacuum to the tissue receiving opening through the strainer;
(g) a first cutter gear;
(e) a second cutter gear, wherein the second cutter gear is configured to cooperate with the first cutter gear to drive movement of the cutter; and
(f) a carriage including a screw opening and a gear receiving portion, wherein the first gear and the second gear are configured to engage the carriage, wherein the first gear engages a cutter gear disposed on the cutter and received within the gear receiving portion of the carriage to rotate the cutter, wherein the second gear passes through the screw opening of the carriage and engages threading disposed within the screw opening of the carriage to translate the carriage, thereby translating the cutter via the cutter gear.

10. The biopsy device of claim 9, further comprising first and second spaced apart seals associated with the body, wherein the first and second spaced apart seals include first and second o-rings.

11. The biopsy device of claim 10 wherein the first and second o-rings are spaced apart to allow for a transverse opening between them.

12. The biopsy device of claim 9 further comprising a tissue sample holder feature disposed proximally of the proximal end of the needle.

13. The biopsy device of claim 9 wherein the needle includes a first lumen and a second lumen, and wherein the cutter is movable within the first lumen.

14. A biopsy device, comprising:
(a) a needle, the needle having a needle axis and a tissue receiving opening;
(b) a cutter moveable relative to the tissue receiving opening in the needle;
(c) a firing assembly operable to fire the needle into tissue, wherein the firing assembly includes a loading mechanism, a firing mechanism, and a needle receiving member extending from the firing mechanism, wherein the loading mechanism is configured to translate proximally to load a portion of the firing assembly, wherein a portion of the firing mechanism is configured to translate distally in response to movement of a cam actuator to fire the needle receiving member distally, thereby firing the needle distally;
(d) a vacuum source, wherein the vacuum source is operable to provide vacuum to the tissue receiving opening; and
(e) a cutter drive mechanism, wherein the cutter drive mechanism includes a carriage, an elongate spur gear, and an elongate lead screw, wherein the cutter drive mechanism is configured to rotate the cutter as the carriage travels along the elongate lead screw relative to the elongate spur gear, wherein the cutter drive mechanism is configured to translate the cutter via the elongate lead screw as the carriage travels along the elongate lead screw relative to the elongate spur gear, wherein the cutter drive mechanism is configured to rotate the cutter via the elongate spur gear as the carriage travels along the elongate lead screw relative to the elongate spur gear, wherein the cutter drive mechanism further comprises a cutter gear fastened to the cutter, wherein the cutter gear is configured to engage the carriage and the elongate spur gear such that the cutter drive mechanism is configured to simultaneously rotate and translate the cutter.

15. The biopsy device of claim 14, further comprising a first spaced apart seal and a second spaced apart seal, wherein the first and second spaced apart seals-includes first and second o-rings.

16. The biopsy device of claim 14, further comprising a first spaced apart seal and a second spaced apart seal, wherein at least one of the first and second spaced apart seals is disposed distally of a proximal end of the needle.

17. The biopsy device of claim 14, further comprising a first spaced apart seal and a second spaced apart seal, further including a tissue sample receiving surface disposed proximally of the first and second spaced apart seals.

* * * * *